US012145110B2

(12) United States Patent
Fischer et al.

(10) Patent No.: US 12,145,110 B2
(45) Date of Patent: Nov. 19, 2024

(54) DOSING DEVICE FOR SOLID MOLDED BODIES FOR PREPARING A SOLUTION

(71) Applicant: Fresenius Medical Care Deutschland GmbH, Bad Homburg (DE)

(72) Inventors: Gerome Fischer, Wesberstedt (DE); Tobias Stöckerl, Tiefenbach (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 724 days.

(21) Appl. No.: 17/057,258

(22) PCT Filed: Jun. 3, 2019

(86) PCT No.: PCT/EP2019/064286
§ 371 (c)(1),
(2) Date: Nov. 20, 2020

(87) PCT Pub. No.: WO2019/233924
PCT Pub. Date: Dec. 12, 2019

(65) Prior Publication Data
US 2021/0331123 A1 Oct. 28, 2021

(30) Foreign Application Priority Data
Jun. 5, 2018 (DE) .......................... 102018004419.0

(51) Int. Cl.
*B01F 21/20* (2022.01)
*A61M 1/16* (2006.01)
(Continued)

(52) U.S. Cl.
CPC ............ *B01F 21/20* (2022.01); *A61M 1/166* (2014.02); *A61M 1/1666* (2014.02);
(Continued)

(58) Field of Classification Search
CPC .................................................. B01F 21/4021
(Continued)

(56) References Cited

U.S. PATENT DOCUMENTS 2,684,782 A * 7/1954 Lime ...................... A47G 19/32
222/230
3,198,402 A * 8/1965 Hunt ......................... A47F 1/03
221/265
(Continued)

FOREIGN PATENT DOCUMENTS

CN 1 659 099 A 8/2005
CN 102 264 610 A 11/2011
(Continued)

*Primary Examiner* — David L Sorkin
(74) *Attorney, Agent, or Firm* — Jacobson Holman PLLC

(57) ABSTRACT

An apparatus for preparing a medical solution by adding substances present in solid molded bodies to a solvent comprises a mixing container, which can be filled through an inlet with a solvent and from which the solution can be supplied to an application via an outlet, and which also has a feed port, through which the solid molded body can be introduced into the mixing container, as well as a dosing apparatus for controllable selective addition of solid molded bodies or parts thereof with different ingredients and/or different concentrations of ingredients from one or more storage containers, in which one or more corresponding receptacles of the apparatus are stored and in which the solid molded bodies are stored in such a way that they can be removed. The apparatus may also have a code detection device for detecting and analyzing a machine-readable code associated with a storage container, said code containing information about which ingredients are contained in the solid molded bodies stored in the respective storage container.

17 Claims, 11 Drawing Sheets

(51) Int. Cl.
*B01F 25/316* (2022.01)
*B01F 33/84* (2022.01)
*B01F 35/21* (2022.01)
*B01F 35/71* (2022.01)
*B01F 35/92* (2022.01)
*B01F 21/00* (2022.01)
*B01F 35/90* (2022.01)
*B01F 101/00* (2022.01)

(52) U.S. Cl.
CPC .......... *B01F 25/316* (2022.01); *B01F 33/848* (2022.01); *B01F 35/2112* (2022.01); *B01F 35/2117* (2022.01); *B01F 35/7141* (2022.01); *B01F 35/71715* (2022.01); *B01F 35/92* (2022.01); *A61M 2205/3327* (2013.01); *A61M 2205/3386* (2013.01); *A61M 2205/3393* (2013.01); *A61M 2205/6054* (2013.01); *A61M 2205/6072* (2013.01); *B01F 21/4021* (2022.01); *B01F 2035/99* (2022.01); *B01F 2101/2202* (2022.01)

(58) Field of Classification Search
USPC .......................................... 422/261, 276, 277
See application file for complete search history.

(56) References Cited

U.S. PATENT DOCUMENTS

| | | | |
|---|---|---|---|
| 3,578,125 A * | 5/1971 | Marlet Barrera | A47J 31/40 194/246 |
| 3,595,786 A | 7/1971 | Horvath et al. | |
| 4,759,907 A | 7/1988 | Kawolics et al. | |
| 5,663,545 A * | 9/1997 | Marquiss | B01L 3/5453 235/375 |
| 5,727,878 A * | 3/1998 | Sullivan, Jr. | B01F 35/4121 366/349 |
| 5,885,446 A * | 3/1999 | McGrew, Jr. | B01F 21/22 210/94 |
| 6,077,484 A * | 6/2000 | Graves | C02F 1/688 422/255 |
| 9,043,019 B2 | 5/2015 | Eliuk et al. | |
| 2004/0047801 A1 | 3/2004 | Petillo et al. | |
| 2006/0259195 A1 | 11/2006 | Eliuk et al. | |
| 2007/0246478 A1 * | 10/2007 | Jarisch | A47F 1/10 221/123 |

FOREIGN PATENT DOCUMENTS

| | | |
|---|---|---|
| CN | 203 780 902 U | 8/2014 |
| EP | 0613688 A1 | 9/1994 |
| WO | WO-9211046 A1 | 7/1992 |
| WO | WO-2018208498 A1 | 11/2018 |

* cited by examiner

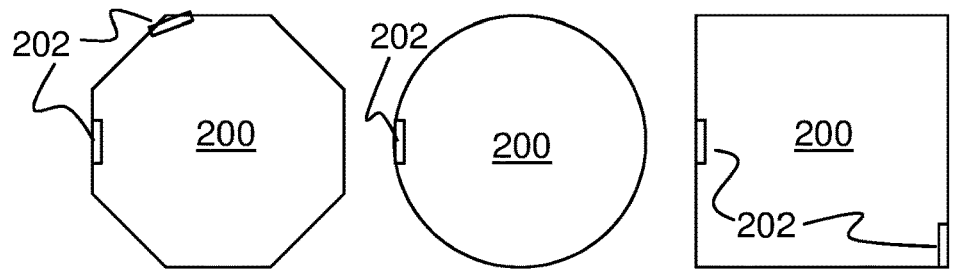
Fig. 2
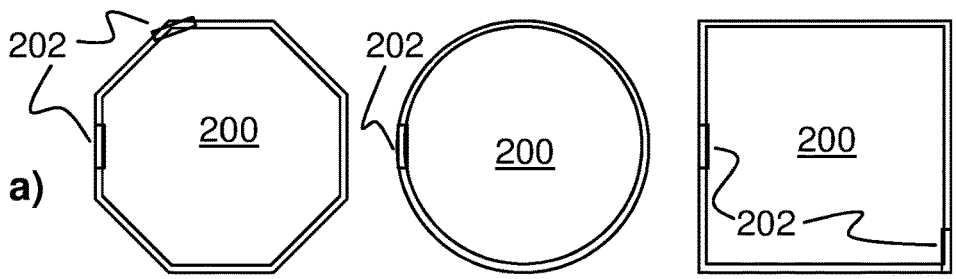
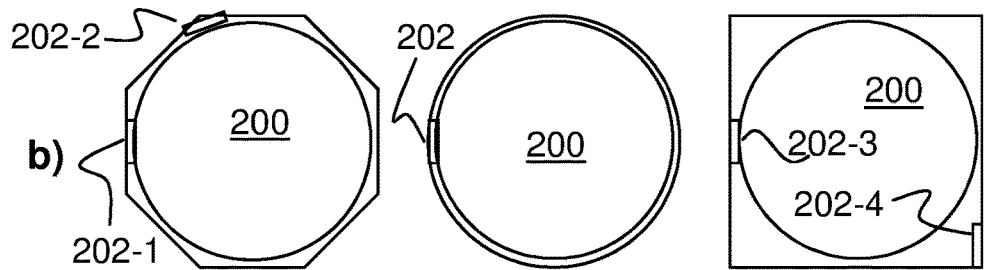
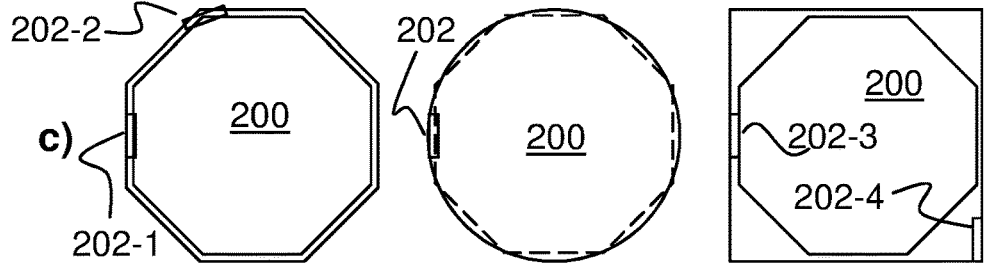
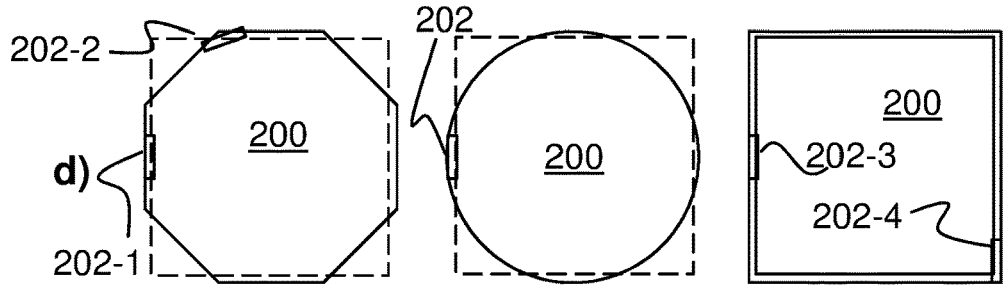
Fig. 3

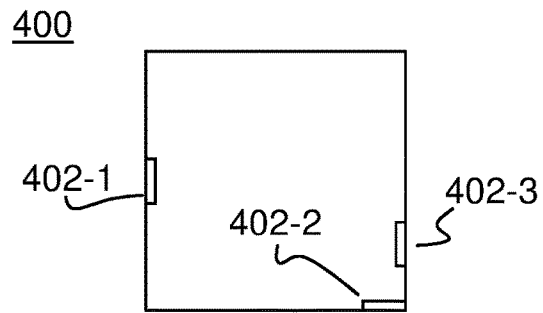
Fig. 4
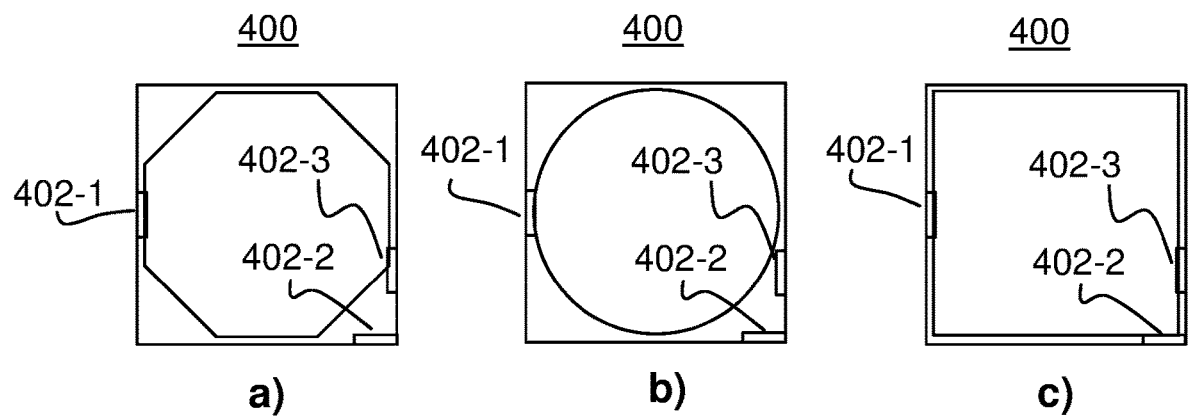
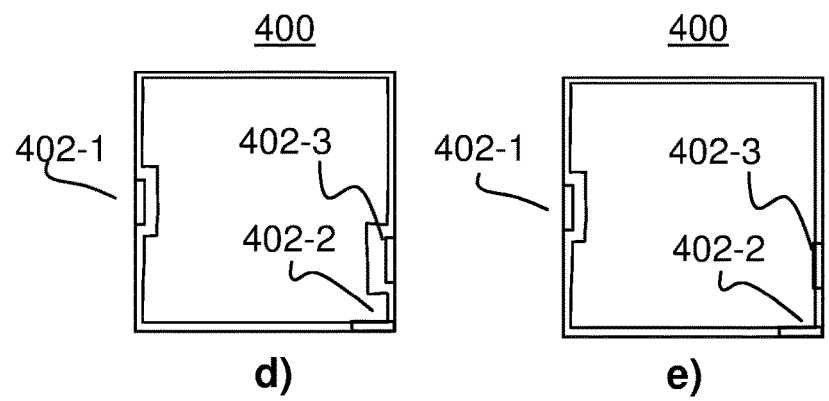
Fig. 5

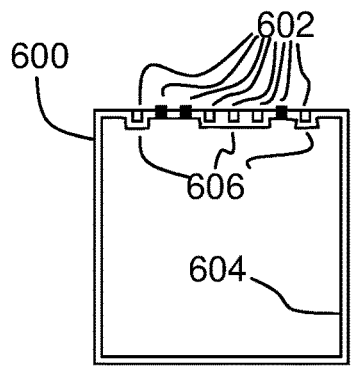
Fig. 6
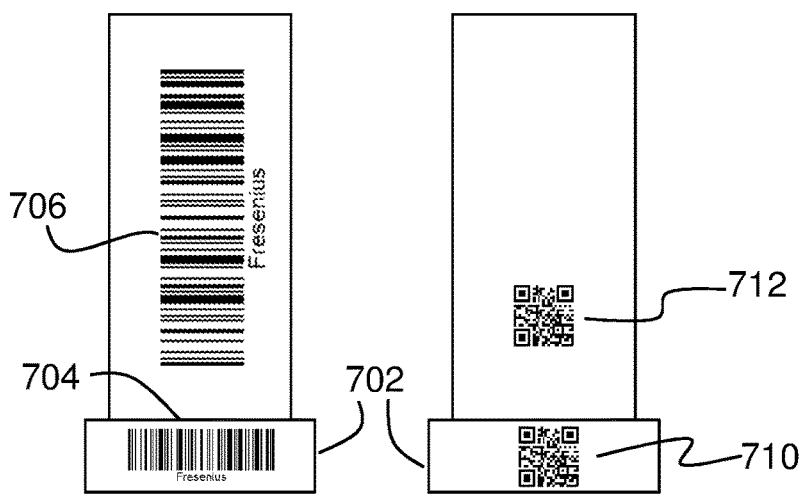
Fig. 7  a)  b)
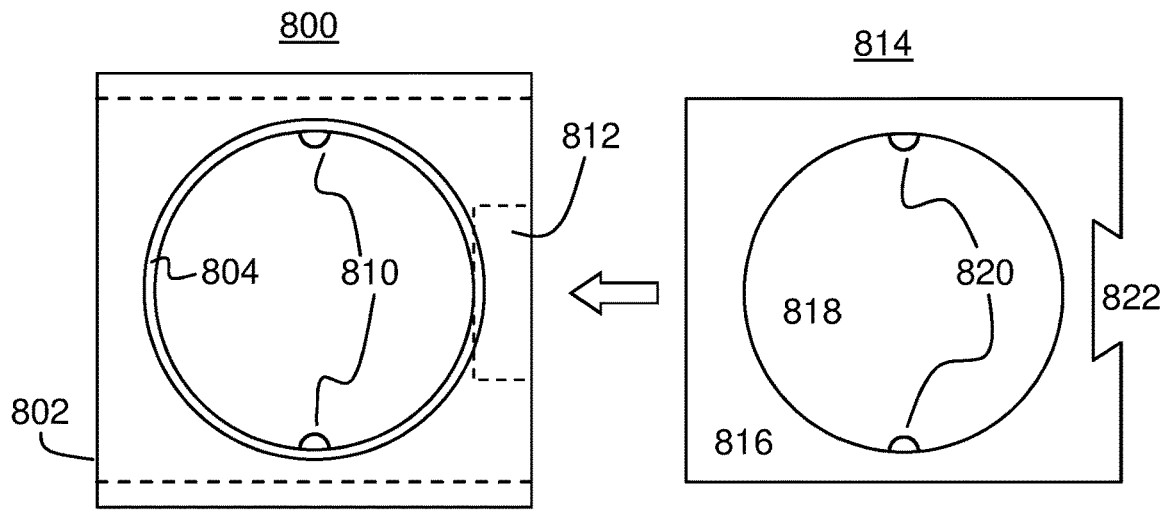
Fig. 8 a)

b)

DOSING DEVICE FOR SOLID MOLDED BODIES FOR PREPARING A SOLUTION

The present invention relates to a dosing device for solid molded bodies or parts thereof for preparing a solution, preferably a medical solution.

STATE OF THE ART

Solutions of substances in the form of solids in a liquid, for example, water, are used in a variety of ways and for a wide variety of purposes. For example, the water in swimming pools is treated with chlorine to kill microorganisms. Chlorine may be added in the form of solid molded bodies or granules to the inflow to the swimming pool, where the solid molded bodies dissolve over a period of time and thereby release chlorine continuously into the water.

The dosing by adding one or more of the solid molded bodies depends on the water volume of the swimming pool and the rate at which the solid body or bodies dissolve and/or disintegrate. In the application described above, it is also necessary to maintain the dose only in a comparatively wide tolerance range, so that if the number of solid bodies during a mixing operation is slightly too high or too low, it will not usually have any problematic effects because the water volume in a swimming pool is usually so much greater. Often the concentration of substance, which added in the form of the soluble solid molded body or bodies, declines over time and must be compensated or balanced, so that individual solid molded bodies of the substance to be dissolved are added at intervals. The molded bodies may also be added manually.

The soluble solid molded bodies for preparing solutions by releasing substances into a solvent such as water may be in the form of tablets. In the case of an automatic apparatus, tablets are removed individually from a storage container by means of an ejector and conveyed into a mixing container, where the tablets dissolve, so that a homogenous solution is obtained after a certain period of time.

Under some circumstances, it is necessary to change the composition of a solution during use. If it is only necessary to change the concentration of the dissolved substances with otherwise the same ingredients present in identical ratios relative to one another, this can be achieved with the known methods and devices by simply adding extra tablets to the mixing container accordingly. If the solution is consumed and is to be prepared continuously or quasi-continuously, i.e., a portion of the solution is removed from the mixing container with the same or variable volume flows and the missing volume is replaced by adding solvent, then the finest possible control of the addition of individual substances is necessary for establishing the proper concentration of substances in the finished solution.

Certain applications in medicine and in dialysis, for example, require an accurate adjustment of the concentrations of various individual substances with comparatively small volumes of a solution to be prepared and under some circumstances require an individual change in the concentration of individual substances during a treatment. Here again, the finest possible control of addition of individual substances is also essential here.

Dialysis is a method for purifying the blood of patients in acute or chronic renal failure. A basic differentiation is made here between methods having an extracorporeal blood circulation such as hemodialysis, hemofiltration or hemodiafiltration (hereinafter combined under term "hemodialysis") and peritoneal dialysis, which does not have an extracorporeal blood circulation.

In hemodialysis, blood is carried in an extracorporeal circulation through the blood chamber of the dialyzer, which is separated from a dialysis fluid chamber by a semipermeable membrane. Dialysis fluid containing blood electrolytes in a certain concentration flows through the dialysis fluid chamber. The substance concentration in the dialysis fluid corresponds to the concentration in the blood of a healthy person. During treatment, the patient's blood and the dialysis fluid pass by both sides of the membrane in countercurrent at a predetermined flow rate in general. Substances that must be eliminated in urine diffuse through the membrane from the blood chamber into the dialysis fluid chamber, while at the same time, electrolytes present in the blood and in the dialysis fluid diffuse from the chamber with the higher concentration into the chamber with the lower concentration.

If a pressure gradient is established on the dialysis membrane from the blood side to the dialysate side, for example, by means of a pump, which withdraws dialysate from the dialysate circulation downstream from the dialysis filter on the dialysate side, water is transferred from the patient's blood, through the dialysis membrane and into the dialysis circulation. This ultrafiltration process leads to the desired removal of water from the patient's blood.

In hemofiltration, ultrafiltrate is taken from the patient's blood by applying a transmembrane pressure in the dialyzer, without any dialysis fluid passing by the side of the dialyzer membrane opposite the patient's blood. In addition, a sterile and pyrogen-free substituate solution may be added to the patient's blood. We speak of predilution or post-dilution, depending on whether the substituate solution is added upstream or downstream from the dialyzer. Mass exchange takes place by convection in hemofiltration.

Hemodiafiltration combines the methods of hemodialysis and hemofiltration. A diffusive mass exchange takes place between the patient's blood and the dialysis fluid through the semipermeable membrane of a dialyzer, and plasma water is filtered through a pressure gradient on the dialyzer membrane.

Plasmapheresis is a method in which blood plasma is separated from corpuscular blood constituents (cells). Separated blood plasma is purified or replaced by a substitution solution and returned to the patient.

In peritoneal dialysis, a patient's abdominal cavity is filled through a catheter inserted through the abdominal wall with dialysis fluid having a concentration gradient with respect to endogenous fluids. The toxins present in the patient's body are transferred through the peritoneum, which acts as the membrane, into the abdominal cavity. After a few hours, the spent dialysis fluid in the patient's abdominal cavity is replaced. Water passes from the patient's blood, through the peritoneum, into the dialysis fluid by osmotic processes, thereby withdrawing water from the patient.

Dialysis processes are usually carried out with the help of automatic dialysis machines such as those distributed by the present applicant under the brand name 5008 or sleep.safe.

The dialysis fluid is either supplied as a finished pre-mix in bags, for example, or is prepared by mixing certain ingredients into water of a medical purity. Dosing of ingredients may be difficult, in particular if a saturated solution is not required.

Pumps of various designs are used for transferring liquids in medical treatment equipment. Peristaltic hose pumps are often used with machines like hemodialysis machines that have an extracorporeal blood circulation. These hose pumps are often used in medical technology because they permit contact-free transport of a liquid. In addition, they supply a flow that is theoretically proportional to the rotational speed, which is independent of the flow resistances upstream and downstream from the pump over wide ranges. In a blood pump in an extracorporeal treatment process, the supply (intake) side is known as the arterial side with an adjusted vacuum of typically approx. −100 to −300 mm Hg column with respect to outside pressure, and the outgoing side is referred to as the venous side with an adjusted excess pressure with respect to outside pressure. Other pumps used in dialysis include impeller pumps, diaphragm pumps or displacement pumps in general, for example, piston pumps, wherein the shape of the displacement element may vary.

One problem with the known processes and devices is that the solution to be prepared for a given volume of the mixing container and/or a given target volume can be prepared only in concentrations that depend on the number of tablets dissolved. This problem can be reduced with known means through only a suitable choice of the respective volume to be established and the respective amount of substances, optionally also different substances contained in a tablet. In doing so, the size of the tablet, i.e., the diameter and thickness, can be adjusted only within certain limits if the dosing apparatus is to be usable for preparing different solutions by means of tablets with different ingredients and/or amounts.

Preparation of a solution with varying concentrations of different substances is not possible at all by addition of tablets with a fixed distribution of ingredients.

Summary

It is therefore desirable to provide a device and a method, which permit more flexible control of the concentration of ingredients of a solution obtained by dissolving solid molded bodies in a solvent, even with varying target concentrations of different ingredients. Furthermore, it is desirable to provide a medical machine or system implementing such a method and/or including such an apparatus.

The term "solid molded body" is used hereinafter as synonymous with the term "tablets" for press-molded, crystalline substances or substances or substance mixtures formulated otherwise or tablets that are present in a solid form and can be dissolved in a solvent.

An apparatus according to the invention for preparation of a medical solution by adding solid molded bodies to a solvent comprises a mixing container that can be filled with a solvent through an inlet, and from which the solution can be sent for use through an outlet. The mixing container, which has a first volume, also has a feed port, through which the solid molded bodies can be introduced into the mixing container. The inlet port and the feed port may be designed separately or as a single opening.

The apparatus also has a dosing apparatus for controllably selective addition of solid molded bodies or parts thereof from one or more storage containers stored in one or more corresponding receptacles of the apparatus, in which the solid molded bodies are stored in a manner such that they can be removed later, into the mixing container.

"Controllably selective" in this context may mean that individual solid molded bodies can be introduced into the mixing container selectively from one or more of a plurality of storage containers. "Controllably selective" in this context may also mean that, when solid molded bodies with different ingredients or different concentrations of ingredients are stored in a known order in a storage container, individual ones of the solid molded bodies that are not available directly as nearest to a removal port of a storage container can also be introduced into the mixing container.

The solid molded bodies stored in a storage container may contain the same or different ingredients. The solid molded bodies stored in a storage container may also contain one or more ingredients in different concentrations and/or mixing ratios. The tablets may be round or polygonal and have a certain defined thickness, at least along a portion of the peripheral edge. Thus, they may have the same thickness everywhere or only along the circumference of the tablet or only along parts of the circumference. To be able to provide different amounts when working with a defined tablet thickness, the tablets may have a reduced thickness or even a hole at the center, for example. If the tablets have intended breaking lines, for example, by having a reduced thickness in certain areas, notches or the like, the other areas may have the same thickness. In any case, the areas of the greatest thickness of the tablet are designed so that, regardless of the relative shifting of two tablets situated one above the other, they cannot become entangled in this displacement. Therefore, two stacked tablets shall in this way always have two or more supporting points or surfaces, which do not penetrate through an imaginary plane between the tablets.

The device may also have a code recognition device for recognizing and analyzing a machine-readable code associated with a storage container. The code contains information about which ingredients are contained in the solid molded bodies stored in the respective storage container. The code may also contain information about the order in which the solid molded bodies stored in the respective storage container are stored if solid molded bodies having different ingredients, amounts, concentrations and/or mixing ratios of ingredients are stored in the storage container.

Each receptacle for storage containers of the apparatus may have an actuator that is releasably connectable to an ejector unit of a storage container accommodating the receptacle. The releasable connection is designed to permit a transfer of force from the actuator to a movable closure piece of the ejector unit in at least one direction.

It is also possible to arrange a plurality of receptacles for storage containers on movable carriers. The carriers may be arranged in a line, displaceably along a trajectory or rotatably on a carousel. In this embodiment, at least one actuator is required, which is operatively connectable to and controllable with a storage container brought by the carrier to a certain position and/or its ejector unit, from which one or more solid molded bodies can be removed. To supply different solid molded bodies, a corresponding storage container is brought to a certain position in each case, so that the actuator can be connected to the corresponding ejector unit to withdraw one or more solid molded bodies from this storage container. Here again, a plurality of actuators may be provided, depending on the embodiment, to permit simultaneous withdrawal of solid molded bodies.

The closure piece may have a first recess or a first punched-out area, which accommodates a single tablet after the latter is removed from the storage container for conveyance into the mixing container or to another location. The first recessed or first punched-out area may correspond to the shape and/or size of the tablet, so that they can be accommodated therein with very little play. The first recess or first punched-out area may also be equipped to limit or prevent rotation of the tablet about a vertical axis during the conveyance process.

A transfer of force in only one direction may comprise, for example, pressing or pushing the ejector unit, wherein retrieval of the ejector unit and the actuator back to the starting position takes place by means of an additional actuator acting in the opposite direction or by means of a corresponding spring force.

A transfer of force in two directions can be achieved, for example, by means of an actuator connected to the ejector in a force-locking or form-fitting connection that can move the ejector in two opposite directions. A form-fitting connection between the ejector and the actuator can be achieved through suitably intermeshing connecting elements, for example, a dovetailed fit. A force-locking connection can be achieved by an electromagnet, for example, acting on a corresponding metallic counterpart.

The ejector unit may be identical to the closure piece or may comprise other components in addition to the closure piece, for example, parts for storage or guidance of the closure piece.

The code detection device for detecting and analyzing a machine-readable code associated with a storage container may comprise means which signal the insertion of a storage container into a receptacle. Such means for detection may comprise one or more electrical, magnetic or optical contacts, for example, which supply a corresponding signal and/or activate a power supply.

The readable code may comprise the shape of the receptacle, which accommodates only storage containers of the corresponding shape of the part to be accommodated by the receptacle. In this case, preferably solid molded bodies with identical ingredients or an identical order of different ingredients is always stored in storage containers having an identical shape. The fitting shapes of the receptacle and counterpart on the storage container and detection of the insertion of such a storage container thus result in an implicit detection of the contents.

The code detection device for detecting and analyzing a machine-readable code associated with a storage container may alternatively or additionally comprise a reader for reading an optical code, a magnetic code or an electric code. Optical readers comprise devices equipped to detect and recognize QR codes or barcodes, for example, or for carrying out optical code recognition (OCR). A corresponding reader, which is directed at a known position of the code on the storage container, may be provided for each receptacle. It is also possible to arrange a single reader, so that it is movable to detect code on one storage container after the other or as needed or to detect a code not applied to a known position on the storage container. It is also possible here to align just one lens unit of the reader with the code on different storage containers instead of aiming the entire reader. The lens may have mirrors, lenses, optical fibers or the like.

Electric readers include, for example, one or more electric contacts, the conditions of which (open/closed) represent a code, near-field communication (NF), radio frequency identification (RFID), devices for measuring resistances, impedances or resonances or the like. The electrical contacts may be operatively connected to conductive imprints or stick-on labels on the storage containers, wherein electrically conductive paths between individual contact pairs may be left open or closed by means of the imprints or stick-on labels and thereby form a binary code. It is also possible to adjust impedances between contact pairs by means of imprints or stick-on labels which form a unique code.

In the case of electrical or optical readers, the receptacles for the storage containers and the corresponding counterparts of the storage containers have identical shapes. When storage containers in which solid molded bodies with different ingredients are stored, can be stored in any receptacle, the device recognizes, on the basis of the code, which ejector is to be triggered in order to add certain ingredients to the solution.

The apparatus may also have one or more units to ensure conveyance of solid molded bodies to an opening having one or more storage containers connected to the apparatus. These units may be equipped to transfer mechanical impacts or vibrations to the storage container, for example, by means of a ram or beater mechanism or by striking the closure piece, the ejector unit or the actuator against a stop. It is also conceivable for the closure piece and a guide, in which the closure piece is guided to be profiled, so that mechanical impacts or vibrations are transferred to the storage container by a movement of the closure piece in the guide. The profiling may comprise, for example, ridged or wavy surfaces.

The mixing container may be a disposable mixing container or a reusable mixing container. The apparatus may have a corresponding holder for removable accommodation of the mixing container. In the case of a disposable mixing container, this may include a plastic bag, which is stored in a holder and has a certain capacity. The holder may be equipped to position the plastic bag in a defined manner relative to the dosing devices.

The holder for the mixing container may have a guide device, which, on insertion of the disposable mixing container into the apparatus, automatically connects or aligns the inlet and the outlet and/or the feed port of the disposable mixing container to corresponding connections or ports in the apparatus in such a way that their function is ensured. In the latter case, it may happen that the mixing container and/or the inlet, outlet and/or feed port is/are not in direct contact with the apparatus and/or the corresponding connections of the apparatus.

In one or more embodiments of the apparatus, it also has a heater for heating the mixing container, a device for creating a flow in the mixing container and/or a device for introducing a gas into the mixing container. Each one of the devices mentioned above may also serve or contribute directly or indirectly toward an improvement in the mixing of the solution and/or the substances introduced into the solution.

In one or more embodiments, the apparatus has a deflecting device, which exerts a force on at least a portion of a solid molded body that is conveyed in one first direction after being removed from the storage container by the closure piece with this force acting in a second direction. The second direction points out of a first plane in which the first direction lies. The deflecting device comes in contact with the solid molded body and becomes active when the closure piece has traveled a certain first distance in the first direction.

The deflecting device may comprise a deflecting lever, which is operated directly or indirectly by the closure piece, or a deflecting ram that is activated by a separate activator and is activated when the closure piece has traveled a certain first distance. In the latter case, a device for determining distance or a signal generator may be provided, supplying a signal when the closure piece has traveled a certain first distance.

Alternatively, the deflecting device may include a stationary portion of the apparatus, which is situated in the delivery path of the closure piece, this portion engaging in a second recess in the closure piece. The second recess then extends from the front side of the closure piece, situated in the first direction, at least up to the first recess or the first punched-out area, in which a solid molded body can be received after being removed from the storage container. The stationary part is to be arranged relative to the first level, so that a force acting in the second direction is exerted on the solid molded body in its conveyance beyond the specific first distance.

The deflecting device can release the entire solid molded body from the first recess or the first punched-out area, so that it can enter the mixing container.

However, the deflecting device can dissolve only the initial portions of a solid molded body from the first recess or the first punched-out area, so that it can enter the mixing container. Two parts of the solid molded body remain in the first recess or the first punched-out area. Therefore, the dosing device or the closure piece can be designed so that the remaining second parts cannot be moved into a second and/or an opposite direction or can be moved only insignificantly. In other words, the second parts of the tablet are more or less secured in the recess or the punched-out area in the closure piece, so that the first parts can be broken off.

The solid molded body can be broken into two or more parts by the deflecting device. A defined division of the solid molded body can be achieved through the use of appropriate intended breaking lines. This partial feed of solid molded bodies allows finer dosing of substances in the solution. Furthermore, breaking up the solid molded bodies also increases their surface area, so that faster dissolving in the solvent can be achieved.

To achieve a targeted division of solid molded bodies along intended breaking lines, it may be necessary to ensure a certain orientation of the solid molded bodies with respect to the first direction during a movement toward the deflecting device. To do so, the solid molded bodies may have a shape, which cooperates with corresponding means of the closure piece and/or the storage container and/or the storage volume. These means may comprise the shape of the tablet and of the storage container and/or the storage volume, which correspond to the recess and/or punched-out area of the closure piece, at least in the area of an opening through which the solid molded bodies are removed from the storage container and/or the storage volume, so that a predetermined orientation of the solid molded body with respect to the first direction is ensured. This can be achieved, for example, by means of a non-circular shape of the solid molded body and a corresponding shape of the storage container and/or storage volume and the punched-out area and/or recess in the closure piece. These means may also include one or more guide ribs in the storage volume and/or storage container as well as the recess and/or punched-out area in the closure piece, which engages in corresponding recesses in the solid molded bodies. If the means are provided both in or on the storage volume and/or storage container and in or on the closure piece, then these are preferably aligned with one another accordingly in a position of the ejector unit and/or closure piece and storage container and/or storage volume, in which a solid molded body is removed from the storage container and/or storage volume.

In one or more embodiments of the apparatus, the dosing device has a selecting unit, by means of which solid molded bodies and/or parts thereof can optionally be conveyed into the mixing container or into another container. The additional containers can receive, for example, solid molded bodies and/or parts thereof that are to be discarded.

This selecting unit may comprise a switch located in the conveyor path and a reversable switch or an ejector, which removes a solid molded body or a part thereof from the conveyor path leading to the mixing container after being removed from the storage container and before being fed to the mixing container. The ejector may apply a mechanical or pneumatic pulse to the solid molded body or parts thereof to be removed from the conveyor path and thereby remove it from the feedstream to the mixing container. For example, it is thereby possible to first convey the first parts of a solid molded body into the mixing container and then to convey second parts of the solid molded body into the additional container. To do so, the movement of the closure piece can be stopped briefly after breaking off the first parts. Then the reversable switch may be switched and/or the ejector activated and then the movement of the closure piece continued and the ejector remains active.

Alternatively, the switch may be replaced by an expanded conveyor path of the closure piece, by means of which a solid molded body or parts thereof can be conveyed into the additional container. The expanded conveyor path may also comprise, in addition to the movement of the closure piece in the first direction, a movement of the closure piece in a third direction. The third direction may be opposite the first direction or may run transversely thereto. The first and third directions may lie essentially in one plane. In this alternative, one part of a tablet may be introduced into the mixing container, for example, by having the closure piece move the tablet in the first direction toward the deflecting device, which separates the part from the tablet. Then the closure piece is moved in the third direction and the remaining part of the tablet is conveyed into the additional container. In this alternative, it also possible to convey whole tablets directly into the additional container, for example, when tablets with different ingredients or concentrations of ingredients are stored in the storage container in a known order and individual ones thereof are not supposed to be introduced into the mixing container.

In one or more embodiments of the apparatus, a detection device is provided, signaling that a solid molded body has been supplied from the storage container to the dosing device. The detection device may comprise the receptacle of a solid molded body in the ejector unit and/or the closure piece by optical means, for example, one or more photoelectric barriers or by electrical means, for example, one or more contacts that are activated directly or indirectly by the solid molded body that is supplied. The detection device may also comprise an arrangement for detecting a weight, a change in weight or a mechanical pulse triggered by a solid molded body. The detection device may be arranged in the ejector unit and/or in the closure piece or it may detect the weight and/or the change in weight of the storage container. In the latter case, it is possible to obtain an absolute determination of the filling level of the storage container. A weight or momentum determination is possible by using a weighing cell, for example.

In one or more embodiments of the apparatus, two or more mixing containers, which are positioned in alternation in relation to the dosing device, so that a solution can be prepared in each, are provided. It is thus possible to prepare two different solutions almost simultaneously or to be always preparing one solution while another solution, already prepared, is being consumed. This permits quasi-continuous operation, wherein a change in the solution composition becomes effective either in switching to the respective other mixing container or the solution composition during consumption of the solution changes as a result of appropriate addition of solid molded bodies.

A storage container in one of the apparatuses described above or variants thereof has a storage volume that holds solid molded bodies in a defined arrangement. A defined arrangement in the sense of the invention means that the solid molded bodies are not stored in a loose, disordered manner in the storage volume, but instead are arranged in a fixed defined manner relative to one another, for example, by being stacked or layered one above the other. A side-by-side arrangement or a similar arrangement is also possible. A defined arrangement also includes a certain order of different solid molded bodies with respect to a withdrawal port in the storage container or storage volume.

The storage container also has an opening through which the solid molded bodies stored in the storage volume can be removed. The opening may be located on the bottom side of the storage volume, for example, when the storage container is placed in a receptacle of the apparatus. The storage volume can be filled through the withdrawal port but a separate filling port may also be provided. Likewise, a ventilation opening, which connects the storage volume fluidically to the surroundings, may also be provided. The ventilation opening may be provided with a filter to prevent the penetration of foreign bodies, fluid molecules of a certain size and the like.

The storage container also has an ejector unit, which is arranged on the opening and is releasably connectable to an actuator of the apparatus. The ejector unit may comprise a closure piece, which is guided movably along a predetermined trajectory and releases the opening of the storage volume in a first position and blocks the opening in one or more second positions along the trajectory that do not correspond to the first position. A solid molded body can be removed from the storage volume through the opening that is released in the first position and can enter a conveyor path, so that it can be conveyed from the ejector unit into the mixing container or discarded. In the second position, no solid molded body exit from the storage volume because the opening is blocked. A blocked opening need not be closed completely, although this may have advantages with respect to protection of the solid molded bodies not yet removed from damage or contamination. It is sufficient if no solid molded body can pass through the opening. The trajectory and/or conveyor path may run in a plane, for example, in two opposite directions along a straight line or a general segment of an arc of a circle. However, the trajectory and/or the conveyor path may also run along a surface of any shape, for example, along an ellipsoidal surface. The ejector unit in one embodiment, for example, the closure piece, can receive a solid molded body that has been removed from the storage volume and convey it to the mixing container of the apparatus along the trajectory or to another container that receives solid molded bodies or parts thereof that have not been used to prepare the solution.

The ejector unit may be permanently or releasably connected to the storage volume. At least the closure piece and/or the part of the ejector unit that conveys the solid molded bodies preferably has/have dimensions adapted to the dimensions and shape of the solid molded bodies. However, it is also possible to design an ejector unit for different shapes and sizes of solid molded bodies. The suitability for blocking and/or releasing the opening in the first position and/or in other positions is also to be taken into account here. If necessary, a corresponding separate part or a separate mechanism for this function is provided to prevent the solid molded bodies from slipping out of the storage volume uncontrollably.

The storage container also has a machine-readable, machine-recognizable and/or machine-analyzable code containing information about which ingredients are present in the solid molded bodies stored in the storage container. The information may indicate which mixing ratios of different ingredients are present in the solid molded bodies, for example, or in which order the solid molded bodies with different ingredients or mixtures of ingredients are stored inside the storage volume with respect to the withdrawal port.

A closure piece of the ejector unit of the storage container may comprise a component having an essentially flat surface at least on a side facing the opening. The component may have a width across the first direction, which goes beyond the width of a solid molded body to be conveyed by the closure piece. A recess or punched-out area, which accommodates a solid molded body for conveyance, may be provided in the component. The component may be solid except for the recess or may have a plurality of interconnected webs forming a space for receiving a solid molded body and at least one area for blocking the opening of the storage container. The component may have a thickness corresponding to that of the solid molded body to be conveyed, at least in the area for blocking the opening of the storage container. At least the top side of the component in this area lies in a plane with the highest elevation of a solid molded body accommodated in the component facing the opening even when the thickness of the component is lower in this area.

The recess or punched-out area may be adapted in shape and/or size to the solid molded body to be accommodated. The recess or punched-out area can completely break through the closure piece or may have at least a partially peripheral edge. In the first case a surface on which the solid molded body can be moved along the trajectory is provided on the side of the recess opposite the opening to the storage volume. In the second case the solid molded body may sit on the edge, and the mechanism is provided for releasing the solid molded body from the recess or from the punched-out area so that the solid molded body or parts thereof can enter the mixing container.

Furthermore, the storage volume may also be equipped so that solid molded bodies can be stored in a certain orientation with respect to one direction in which they are moved after being withdrawn. To do so, guide ribs or webs, which correspond to corresponding recesses in the solid molded bodies, may be provided inside the storage volume. In the case of solid molded bodies having a shape that is not rotationally symmetrical, the storage volume may also be adapted to the nonrotationally symmetrical shape so that the orientation of the solid molded bodies is defined when they are removed.

The recess or punched-out area of the closure piece may be equipped accordingly to receive the solid molded bodies in the defined orientation. This embodiment may be advantageous when solid molded bodies are provided with one or more intended breaking points and even parts of solid molded bodies are also dosed.

In one embodiment, the apparatus and the storage container are equipped to guide the closure piece along a trajectory having a first section that serves to convey a solid molded body or a part thereof into the mixing container and also having a second section that serves to convey a solid molded body or a part thereof into another container. The additional container receives solid molded bodies or parts thereof that are not used to prepare the solution.

The first and second sections of the trajectory may be separated from one another by the first position on the trajectory. Starting from the first position, a solid molded body or parts thereof may thus be conveyed into the mixing container, for example, in a first direction by conveyance along the first section of the trajectory. If the solid molded body is to be conveyed into the additional container, it is conveyed along the second section of the trajectory, for example, in a direction opposite the first direction or in a direction transversely thereto, starting from the first position.

The closure piece can be moved by the actuator of the apparatus in a linear or curved movement along the trajectory. The linear or curved movement may be in a plane essentially perpendicular to the vertical axis of the storage container accommodated in a receptacle in the apparatus.

Furthermore, the storage container may be equipped to act on solid molded bodies stored inside the storage volume with a force directed toward the opening. For example, this may be accomplished through corresponding spring means or fluids under pressure. Alternatively or additionally, the storage volume may have a device, which is permeable at least for gaseous fluids and connects a space formed by solid molded bodies that have been removed to the ambient atmosphere. This device may optionally comprise a ventilation opening equipped with a filter, a fluid-permeable membrane or the like.

In addition, the storage container may also have a transparent or translucent region at least in an area of the storage volume that allows visual or optical monitoring or detection of a filling level of the storage container or at least detection of the fact that the fluid level has dropped below a predetermined fluid level. The optical control may take place by means of optical sensors, for example, a camera or one or more photoelectric barriers, which emit a signal that represents the filling level or indicates that the filling level has dropped below the predetermined filling level. Alternatively or additionally, the storage container may be equipped to emit an electric signal representing the filling level or indicating that the filling level has dropped below the predetermined filling level. To do so, one or more electric contacts, for example, may be provided in different locations inside the storage volume, or a capacitive or ultrasonic sensor or the like may be provided.

The apparatus may be used to prepare any solutions, in which the concentration of individual ingredients must be adjusted variably either individually or over a period of time. The apparatus is suitable in particular for preparing medical solutions for treatment of acute or chronic renal illnesses, for example, dialysis fluid (dialysate), which is used for treatment of acute or chronic renal diseases.

A method for preparing a solution using the apparatus described above is described below, wherein it is assumed that the mixing container already contains a certain amount of solvent, such as water. The water may be in the form of high-purity water, for example, which has been obtained from tapwater by filtration or other methods. However, it is also conceivable that one or more solid molded bodies are introduced first into the mixing container before the solvent is added.

First, the apparatus must be prepared by inserting one or more storage containers into the receptacles provided for them. The code recognition device of the apparatus is triggered in this context to detect the insertion of the storage containers and/or to recognize and analyze the machine-readable code on the storage container(s). The code is thus detected during or after insertion of a storage container, and corresponding signals describing and representing the contents of the storage container are generated and supplied for use in a control unit. After detection and recognition, it is known in which storage container solid molded bodies are stored, with which ingredients and/or in which order different solid molded bodies are stored in a storage container. The apparatus is also triggered to receive a signal conveying information about an amount and/or a volume of solvent, which is present in the mixing container and is used to prepare the solution. This signal can be received via a user interface, but it is also possible to generate a corresponding signal by means of a measurement device and to transmit it to the apparatus. Suitable measurement devices include flowmeters, for example, which determine the amount and/or corresponding volume introduced into the mixing container and optionally the amount and/or corresponding volume removed from the mixing container or measurement devices for determining the weight of the mixing container and/or for determining the amount of solvent present in the mixing container after subtracting the known inherent weight of the mixing container and optionally taking into account the specific gravity of the solvent for determining the amount of solvent present in the mixing container. Other measurement means comprise floats connected to a measured value pickup or sensor for detecting the liquid level in the mixing container, which allows a determination of the volume contained in the mixing container, based on the known geometry thereof and/or its course over the filling height. Instead of one or more floats, the liquid level may also be determined by means of sound waves, beams of light or electromagnetic beams in general. It is also possible to determine the amount of solvent by identification of the mixing container and to supply a corresponding signal. This is possible, for example, when mixing containers prefilled with a certain volume and/or a certain amount of solvent are used.

The apparatus is also triggered to receive a signal representing a target composition of the finished solution. The signal can be received, for example, over a user interface or a communications interface which supplies a communications link to a computer.

To prepare the solution, the apparatus is triggered to convey one or more solid molded bodies and/or parts thereof out of one or more of the storage containers inserted into the apparatus and into the mixing container. Parts of solid molded bodies can be supplied by dividing whole solid molded bodies and selectively supplying some parts and/or discarding other parts. If different solid molded bodies are stored in a storage container, selected ones can be conveyed into the mixing container, while other ones not needed for preparation of the solution can be conveyed into another container. The selection and quantity of solid molded bodies or parts thereof conveyed into the mixing container for preparation of a solution depend on the desired composition and concentration of the solution.

In one embodiment of the apparatus, a mixing container is provided for a one-time use and is already filled with a basic quantity of substances required to prepare solutions. Addition of the same or additional additives beyond the basic amount for preparing the desired solution is accomplished through appropriate control of the apparatus in a manner similar to that described above. The apparatus is equipped and controlled for receiving signals that represent information about the mixing containers used with different basic quantities of optionally different substances. The signals may be received over a user interface or by detection and readout of a machine-readable code associated with the mixing container. Knowledge of the basic quantity of substances present in the respective mixing container makes it possible to determine the required quantity of substances to be added and to control the apparatus accordingly.

In one embodiment of the apparatus, a certain quantity of the solution prepared is removed from the mixing container continuously or in intervals. Accordingly the quantity removed may be replaced continuously or in intervals by addition of solvents and solid molded bodies in a suitable amount and composition. The apparatus may therefore have one or more measurement devices, which determine the composition of the solution contained in or removed from the mixing container. Signals generated by the one or more measurement devices are sent to a control unit of the apparatus, which compares the actual composition of the solution with the target composition and controls the feed of solid molded bodies and/or solvent accordingly. Starting from a known initial composition and quantity, information about the quantity of solution removed may also be used to determine the necessary amount of solvent to be resupplied and the type and number of solid molded bodies to be added and to generate the proper signals, which are sent to the control unit of the apparatus.

Due to the possibility of introducing different ingredients separately, it is possible to prepare a solution with a wide range of variation in the concentration of different substances in the solution by using the apparatus described above and the corresponding method.

If the apparatus is located directly at the site of use of the solution, this simplifies the logistics and warehousing because it is not necessary to keep finished solutions with different compositions on hand in storage. Furthermore, it is possible to provide solutions with individual compositions for an even greater number of different fields of use or application cases.

Another advantage of the present apparatus and the present method is the possibility of adjusting a solution in the course of its use, for example, adjusting the composition of dialysate during a dialysis treatment to the needs of the patient. Thus, for example, potassium removed from a patient's blood circulation by dialysis, which can result in an unwanted change in the patient's heart rate, can be returned to the patient by appropriate adjustment of the potassium concentration of the dialysate and/or if an imminent drop in potassium level is detected promptly and at an early point in time, this can be counteracted through appropriate adjustment of the potassium concentration of the dialysate.

BRIEF DESCRIPTION OF THE DRAWINGS

The apparatus is described below with reference to the drawings, in which:

FIG. 2 shows a first example of a choice of molds of receptacles for storage containers with devices for detecting coding of storage containers accommodated therein, FIGS. 3 *a*)-*d*) show examples of detection of storage containers inserted correctly or incorrectly into receptacles according to FIG. 2, FIG. 4 shows another example of a receptacle with devices for detection of coding of storage containers accommodated therein, FIG. 5 shows examples of detection of storage containers inserted into the receptacle according to FIG. 4, FIG. 6 shows another example of a receptacle with devices for detection of coding of storage containers accommodated therein, FIG. 7 shows schematic diagrams of storage containers with variants of machine-readable codes, FIG. 8 shows components of a first example of an ejector unit.

The same or similar elements may be represented with the same reference numerals in the figures.

DESCRIPTION OF EMBODIMENTS

Figure 1:
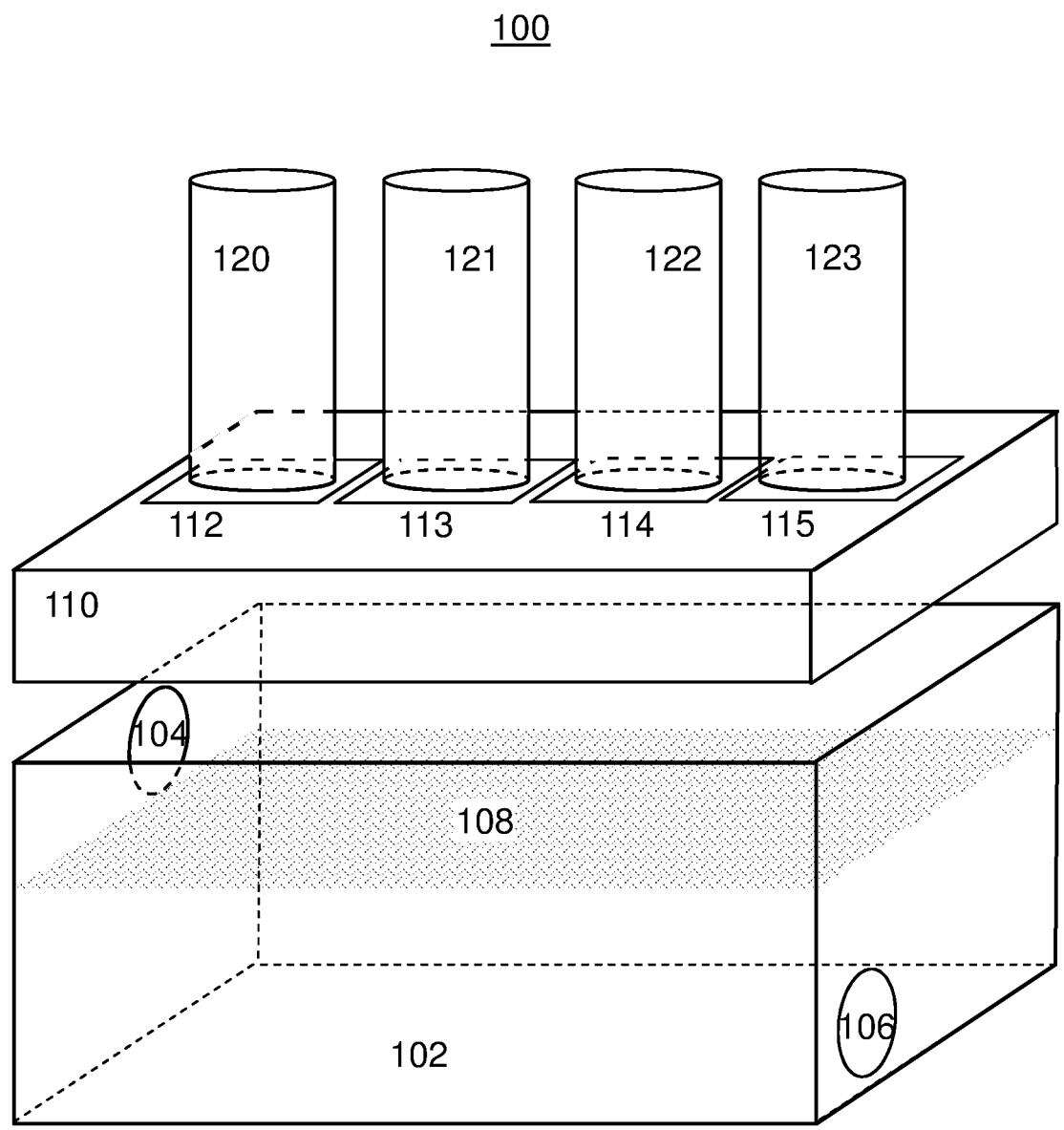
FIG. 1 shows a first schematic diagram of an example of an apparatus for preparing a solution.

FIG. 1 shows a schematic diagram of an example of an apparatus 100 according to the invention for preparing a solution. Apparatus 100 comprises a mixing container 102 having an inlet 104 and an outlet 106. A solvent can be added to the mixing container 102 through the inlet 104, and a prepared solution can be discharged through the outlet 106 for use. The figure shows the mixing container 102 filled with a liquid solvent, as indicated by the surface 108, which is drawn with wavy lines, up to a lower edge of the inlet 104. A cover part 110—shown at a distance from the mixing container 102 in the figure—has four receptacles 112-115, into which storage containers 120-123 are inserted. Receptacles 112-115 are represented by squares, shown in perspective in the figure, and are not illustrated in detail. Solid molded bodies (not shown in the figure) stored therein can be removed selectively from the storage containers 120-123 and conveyed into the mixing container 102. The solid molded bodies conveyed into the mixing container 102 dissolve in the solvent contained in mixing container 102 and thus create a solution with the desired composition. When the solution has the desired composition, it can be removed through the outlet 106 and sent for use. Inlet 104 and/or outlet 106 may also be connected to cover part 110, for example, by tubes or pipes, which lead into and out of the mixing container.

A control circuit (not shown in the figure) comprises one or more processors, working memories and nonvolatile memories, which store computer program instructions, so that they can be retrieved and form a control program for preparing a solution by means of the apparatus. The control circuit and the respective components may be arranged in or on the cover part 110. Means (also not shown in the figure) for detecting a code provided on the storage containers 112-115 also provide information about the solid molded bodies stored in the respective storage containers 112-115 in a machine-readable form.

FIG. 2 shows a first example of a choice of shapes of receptacles 200 for storage containers (pedestal shapes) with code detection devices 202 for detecting a code on storage containers accommodated therein. Receptacle 200 shown at the left of the figure has an octagonal outline, which is provided for receiving a corresponding octagonal base part of a storage container. Devices 202 may be simple switches, for example, which are in a different condition, e.g., closed, when a storage container is inserted than when the storage container is not inserted and they are open, for example. Instead of simple switches, a magnetic switch or a photoelectric barrier may also be provided, or something similar that will provide the corresponding signals.

Receptacle 200, shown at the center of the figure, has a round cross section, which is provided to receive a corresponding round base part of a storage container. With this receptacle, only one device 202 is provided, as will be explained further below with reference to FIG. 3.

Receptacle 200 shown at the right of the figure has a square cross section, which is provided for receiving a corresponding square base part of a storage container. Two devices 202 are provided with this receptacle, as with the octagonal receptacle.

FIG. 3 shows examples of detection of storage containers inserted correctly and incorrectly into the pedestal according to FIG. 2.

Part a) of FIG. 3 shows storage containers with the correct base parts inserted into the proper receptacles, represented by the corresponding shapes with slightly smaller dimensions than the receptacles. Thus, a storage container with an octagonal base part is accommodated in the left receptacle 200, a storage container with a round base part is accommodated in the central receptacle, and a storage container with a square base part is accommodated in the right receptacle. The signal status of the respective devices 202 is altered in comparison with the signal status when no storage container is accommodated. For example, all the switches accommodated in a respective receptacle are now closed. The code for the contents of the storage containers is based on the shape of the base part, i.e., solid bodies with certain ingredients and optionally in a certain concentration are stored in a storage container with a base part of a certain shape. For detecting the ingredients, it is sufficient to detect the insertion of a storage container with the correctly shaped base part. The code for the shape of the base part also has the advantage for the user that the correct receptacle for a given storage container is easily recognizable. In addition, a color code may also be provided. A sequence of storage containers predetermined by the shape of the respective receptacle may be advantageous in some embodiments of the apparatus.

In part b) of FIG. 3, a storage container with a round base part is inserted into each of the receptacles. Thus, the wrong storage container has been inserted into the receptacles with an octagonal cross section or with a square cross section. In the octagonal receptacle, the round base part causes only the signal status of the device 202-1 to be altered, i.e., for example, a corresponding switch is closed. Device 202-2 is arranged in such a way that the round base part of the inserted storage container does not change its signal status. It is thus possible to recognize that a storage container with a non-octagonal base part has been inserted and a corresponding signal can be generated. The signal may be used to notify the user that a storage container not intended for this receptacle has been inserted.

A storage container with the correct base part has been inserted into the receptacle with the round cross section, so this does not result in a change in comparison with part a) of FIG. 3.

The storage container with the round base part inserted into the receptacle with the square cross section results in the signal status of device 202-3 being altered, for example, a corresponding switch is now closed but the signal status of the device 202-4 does not change. It is thus possible to recognize that a storage container having a non-square base part has been inserted, and a corresponding signal can be generated. Here again, the signal may also be used to point out to the user that a storage container not intended for this receptacle has been used.

The situation illustrated in part c) of FIG. 3 is similar to that in part b). In deviation from the situation described previously, in this case, storage containers with an octagonal base part have been inserted into the receptacles with octagonal and square cross sections. The octagonal base part does not fit in the receptacle with the round cross section, as indicated by the diagram with a dotted line. As described previously for the case of a storage container with a round base, by inserting a storage container with an octagonal base, only the signal of device 202-3 of the receptacle with the square cross section changes and the signal status of the device 202-4 remains unchanged. It is thus possible to recognize that a storage container having a non-square base part has been inserted and a corresponding signal can be generated. The signal may also be used here to point out to the user that a storage container not intended for this receptacle has been inserted.

Part d) of FIG. 3 again illustrates a situation similar to that in part b), but in deviation from the situation described previously, this shows a storage container with a square base part inserted into the receptacle with a square cross section. The square base part does not fit into the receptacles with the octagonal or round cross sections, as indicated by the diagram with the dotted line. In this case only the correct insertion of a storage container with a square base into the proper receptacle can be recognized.

FIG. 4 shows another example of a receptacle 400 with devices 402-1, 402-2 and 402-3 for detection of code for storage containers accommodated therein. In contrast with the receptacles described previously, only one receptacle with a single cross section is provided, but it has three devices 402-1, 402-2 and 402-3 for detection of code for storage containers accommodated therein instead of having one or two devices. Devices 402-1, 402-2 and 402-3 are arranged in receptacle 400 in such a way that detection of storage containers with different base parts is possible. If an apparatus for preparing a solution has a plurality of such receptacles, i.e., a fixed sequence or position of the storage containers inserted with respect to the arrangement of the receptacles is not necessary.

Detection of different storage containers with different base parts will now be explained with reference to FIG. 5. Part a) of FIG. 5 shows a storage container having an octagonal base part inserted into the receptacle 400. The signal statuses of devices 402-1 and 402-2 are altered in comparison with the signal status when no storage container is being accommodated, e.g., corresponding switches are now closed. The signal status of the device 402-3 is unchanged.

Part b) of FIG. 5 shows a storage container having a round base part inserted into the receptacle 400. The signal status of device 402-1 has changed in comparison with the signal status when no storage container has been accommodated, for example, a corresponding switch is now closed. The signal status of devices 402-2 and 402-3 has not changed.

Part c) of FIG. 5 shows a storage container with an octagonal base part inserted into receptacle 400. The signal statuses of all the devices 402-1, 402-2 and 402-3 have changed in comparison with the signal status when no storage container has been accommodated, for example, corresponding switches are now closed.

Part d) of FIG. 5 shows a storage container with a square base part with recesses, inserted into the receptacle 400. The signal status of the device 402-2 has changed in comparison with the signal status when no storage container was accommodated, for example, a corresponding switch is now closed. The signal statuses of devices 402-1 and 402-3 are not changed.

Part e) of FIG. 5 shows another storage container with a square base part with recesses, inserted into the receptacle 400. The signal statuses of devices 402-2 and 402-3 have changed in comparison with the signal status when no storage container is accommodated, for example, the corresponding switches are now closed. The signal status of the device 402-1 has not changed.

The combination of signal statuses of the devices 402-1, 402-2 and 402-3 makes it possible to deduce the shape of the base part of the storage container accommodated therein, and when there is a unique association between the shape of the base part and the contents of the storage container, it is also possible to deduce the contents.

FIG. 6 shows another example of a receptacle 600 with devices 602 for detecting a code on storage containers accommodated therein. In this example, eight devices 602 for detecting a code on storage containers accommodated therein are arranged along one side of the receptacle with a square cross section. Devices 602 are represented by rectangles as an example, some of which are shown with black filling and some are shown without any filling. The devices may include switches, for example, each of which can assume an open condition and a closed condition, and therefore, in their entirety, may constitute a binary code. A storage container 604, represented by the internal frame in the figure, is inserted into receptacle 600. The base part of the storage container 604 is provided with bays on the side facing the devices 602, these bays bringing the devices 602 situated in the area of bays 606 into a first condition when inserted. Devices situated in areas outside of bays 606 are brought into a second condition. When the devices include switches, they may be open in the area of the bays, for example, and closed in areas outside of the bays. This is illustrated in the figure by the different type of filling of the rectangles representing devices 602. The code shown as an example in the figure, representing eight devices 602, can be represented in binary form as 01100010, so that on the whole, 256 different codes can be represented with eight devices 602 in the figure.

FIG. 7 shows schematic diagrams of storage containers 700 with additional examples of variants of machine-readable codes. Part a) of this figure shows a machine-readable barcode 704 applied to the base part 702 of the storage container 700. When inserted into the receptacle or in the inserted condition, barcode 704 can be read by a reader (not shown in the figure) arranged in the corresponding receptacle, and a signal representing the information contained therein can be sent to a control device of the apparatus for preparing the solution. Barcode 704 can also be read out by a reader not arranged in the receptacle, for example, a portable reader, which is connected by signal to the device for preparing the solution or to a reader arranged in the certain area of the apparatus for preparing the solution. Barcode 706 can also be read out by such a reader, expediently prior to the insertion of the storage container into the corresponding receptacle. In this case, detection of the fact that a storage container has been inserted into a receptacle may be necessary in order to create an association of the receptacle and the storage container and/or the contents of the storage container from the sequence of readout of the barcode and detection of the insertion of the storage container into the receptacle. In part b) of the figure, the barcodes have been replaced by two-dimensional codes 710, 712, represented by QR codes in the figure. The preceding discussion applies to detection and allocation accordingly.

FIG. 8 shows components of a first example of an ejector unit of a storage container of the apparatus for preparing a medical solution. The left part of the figure shows a top view of a storage container 800 having a base part 802 and a storage volume 804. The storage volume 804 has two webs 18 arranged on the inside, serving to position solid molded bodies stored in the storage volume with respect to the base part 802. The storage volume 804 is open on the bottom side, i.e., on the side abutting against the base part 802. The base part 802 illustrated as an example in the figure is a right-angle parallelepiped (cube) open on the right and left sides, like the shell of a matchbox. The dotted lines on the top and bottom sides of the base part represent the inner borders of the side walls of the parallelepiped. The area on the right side of the base part, shown with dotted lines, is a recess 812 in the lower surface of the base part, by means of which an actuator of the apparatus for preparing a solution (not shown in the figure) can be connected to the ejector unit. A closure piece 814 (shown on the right side of the figure) can be inserted movably into the hollow base part 802 of the storage container 800. The arrow indicates the direction in which the closure piece 814 can be inserted into the base part 802. Closure piece 814 has a recess or punched-out area 818, in which a solid molded body can be accommodated in the base body 816. The recess or punched-out area 818 has two protrusions 820, which correspond in a certain position of the closure piece 814 to the storage volume with the webs 18 of the storage volume and hold a solid molded body accommodated in a defined position therein. It should be pointed out that the ejector unit may also be designed without the webs 18 and protrusions 820. A dovetailed depression 822, into which an actuator of the apparatus (not shown in the figure) can be inserted from beneath through the recess 812, is arranged on the right side of the closure piece 814.

Figure 9:
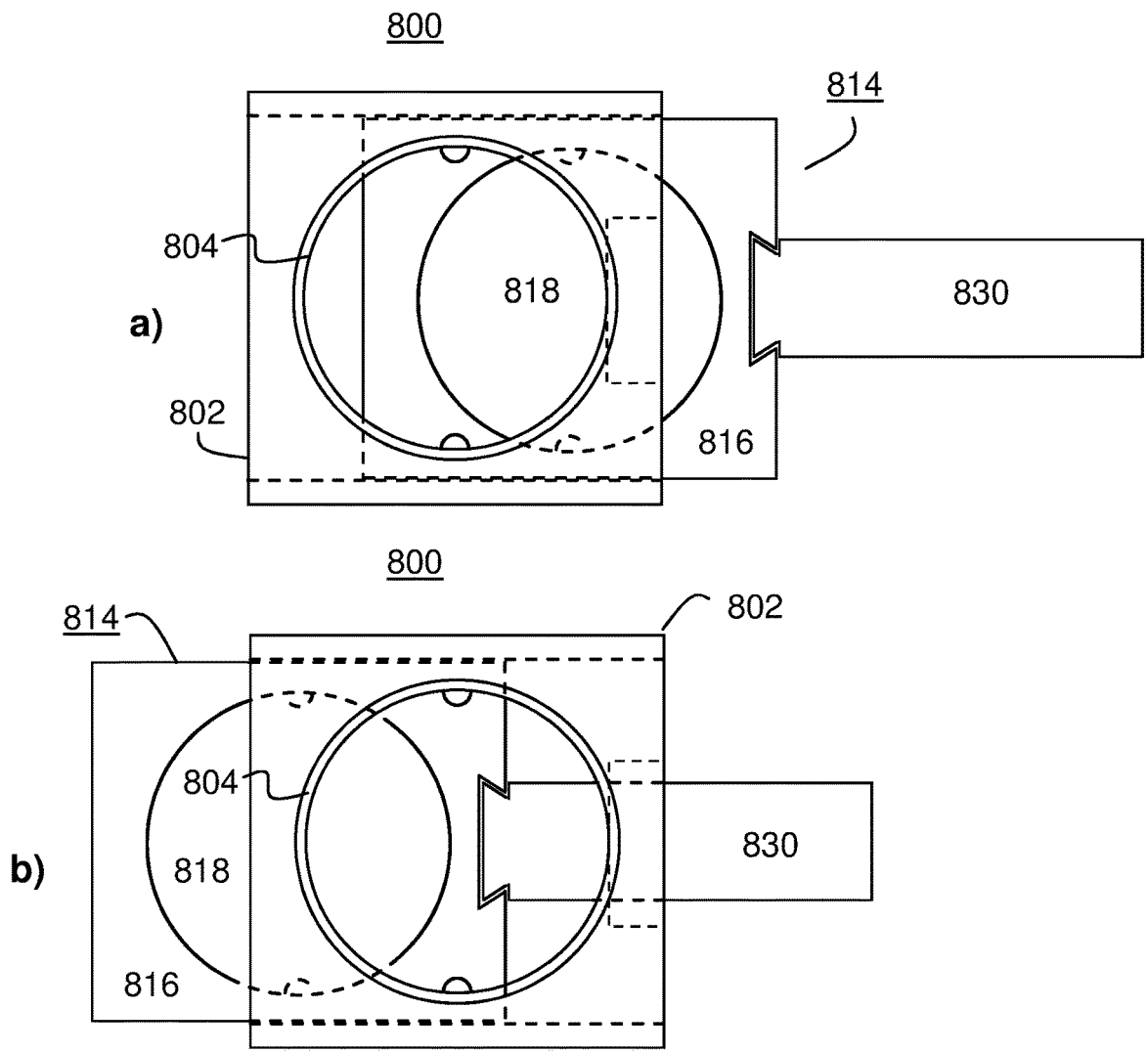
FIG. 9 shows the ejector unit from FIG. 8 in various working positions.

FIG. 9 shows the ejector unit from FIG. 8 in various working positions. In part a) of the figure the closure piece 814 is shifted out of a central position to the right out of the base part 802 of the storage container 800. Base part 802 in this example is connected by a dovetailed connection to an actuator 830 so that a back and forth movement of the actuator 830 in a plane is transferred to the closure piece 814. The part of the base body 816 of the closure piece 814 opposite the actuator 830 is situated in the area in which the opening in the storage volume 804 is located and blocks it so that no solid molded body can leave the storage volume 804. A solid molded body (not shown in the figure), which was optionally previously accommodated in the recess or the punched-out area 818 of the base body 802, is moved away by the closure piece 814.

In part b) of the figure, the closure piece 814 has been shifted out of a central position to the left out of the base part 802 of the storage container 800. In this position, the area of the base body 816 of the closure piece connected to the actuator 830 as well as the actuator 830 itself blocks the opening of the storage volume 804, so that no solid molded body can leave the storage volume 804. A solid molded body (not shown in the figure) optionally previously accommodated in the recess or punched-out area 818 of the base body 802 is moved along together with the closure piece 814.

A solid molded body accommodated in a recess or punched-out area 818 of the base body 802 can be pushed out of the base part 802 of the storage container 800 with a further shift to the left or right and can then leave the recess or punched-out area 818. Depending on the embodiment, shift in a first direction may convey a solid molded body accommodated in a recess or punched-out area 818 of the base body 802 into a mixing container, and a shift in another direction can be used to convey the solid molded body into another container.

Figure 10:
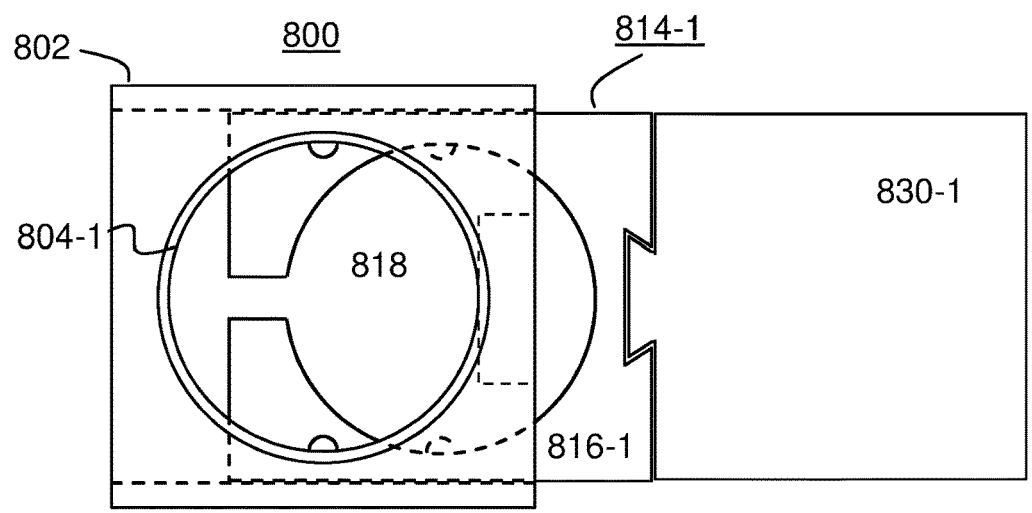
FIG. 10 shows a second example of an ejector unit.

FIG. 10 shows a second schematic diagram of an exemplary ejector unit of a storage container 800-1, representing a modification of the ejector unit described in conjunction with FIG. 9. In this modification, actuator 830-1 has a width corresponding to that of the closure piece 814-1. Improved blocking of the opening of the storage volume 804-1 can be achieved in this way and also offers better protection for the solid molded body remaining in the storage volume 804-1. Furthermore, the base body 816-1 has a slot on the side opposite the actuator 830-1 into which deflecting means (not shown in the figure) in which they can engage, deflecting a solid-state molded body or parts thereof into a certain direction out of the deflection plane.

Figure 11:
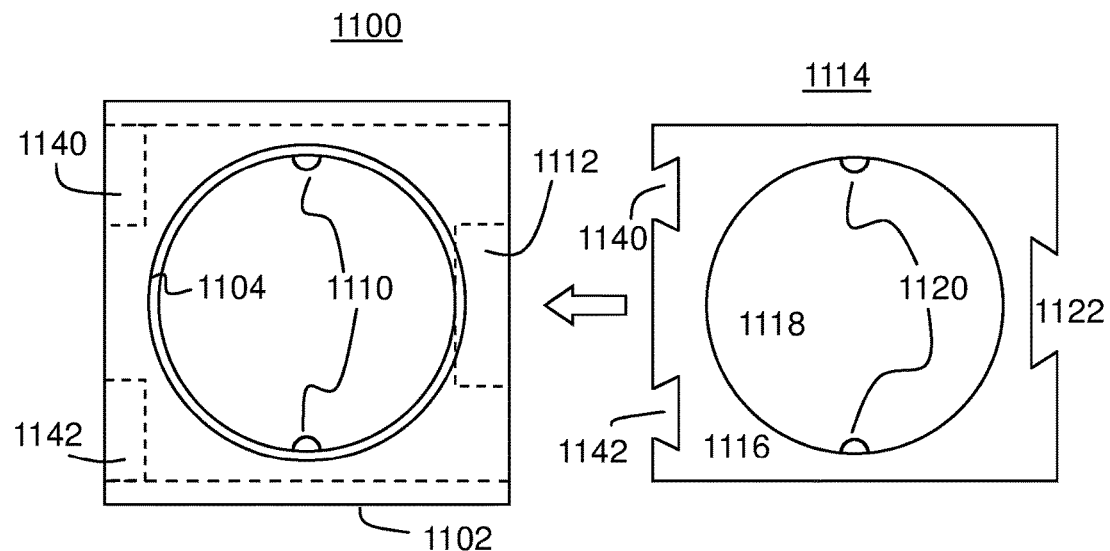
FIG. 11 shows components of a third example of an ejector unit.

FIG. 11 shows a second schematic diagram of components of a third example of an ejector unit of a storage container 1100. The components shown in the figure correspond essentially to those described with reference to FIG. 8. In contrast with that, two other recesses 1140 and 1142 are provided in the lower surface of the base part at the left side of the base part 1102 and can be connected to corresponding connecting elements 1144 and 1146 of closure piece 1114 by means of connecting elements of an expansion element.

Figure 12:
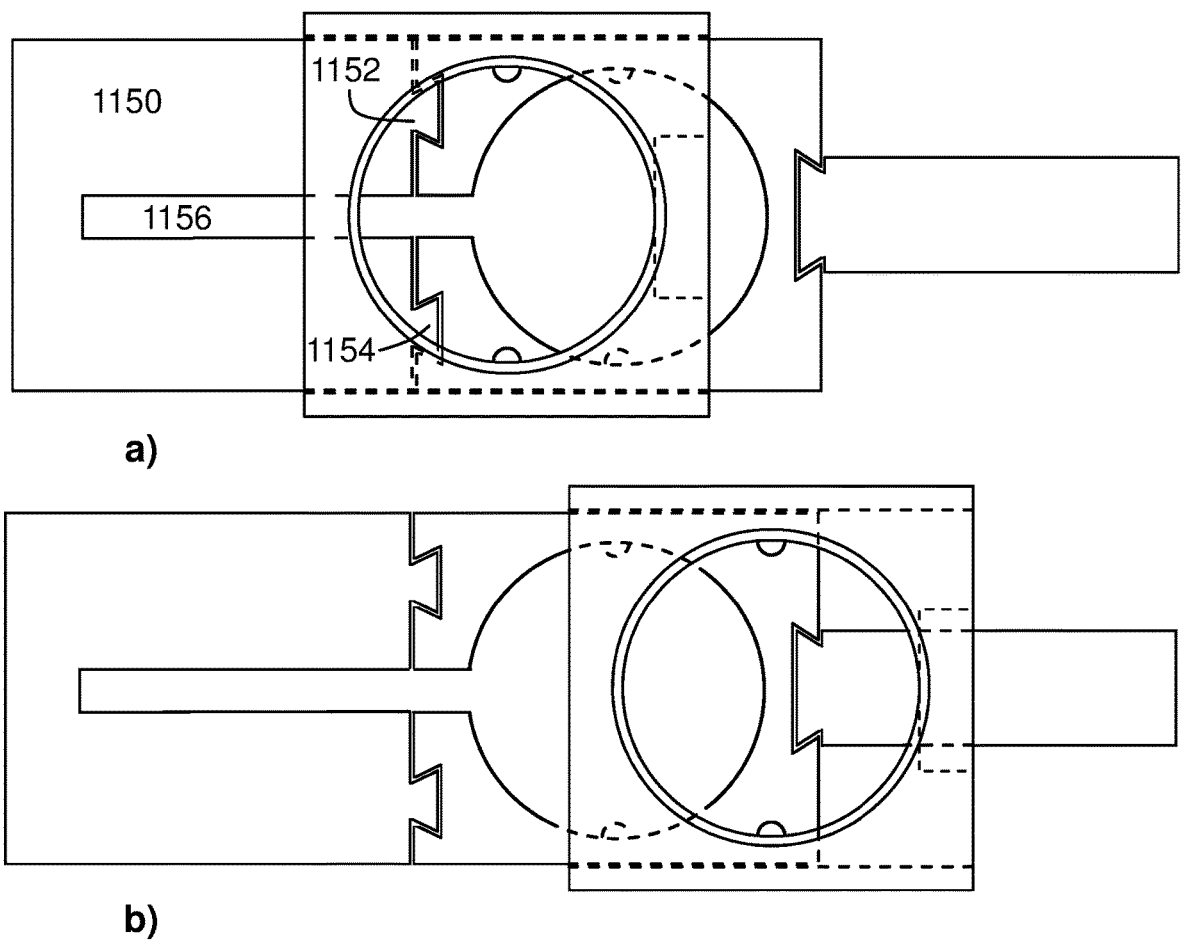
FIG. 12 shows the ejector unit from FIG. 11 in different working positions.

FIG. 12 shows components of the ejector unit of the storage container 1100 presented in FIG. 11 with the connected expansion element 1150 in various positions. Expansion element 1150 has dovetailed components 1152 and 1154 which engage in coupling elements 1144 and 1146 of the closure piece 1114. It is pointed out that with the ejector unit shown in this figure but also in other variants presented in this description, other types of connections are also possible instead of the dovetailed connection, for example, the other connections may use differently shaped intermeshing connecting elements that are releasably engaged in a form-fitting manner or magnets or electromagnets or the like. It is also possible to bring an actuator into contact with the closure piece without connecting them and to have it act in only one direction. Any movement in the other direction may be induced, for example, by a spring force acting on the side of the closure piece opposite the actuator.

In part a) of the figure, the closure piece 1114 has been pulled out of its central position toward the right by actuator 1130. Expansion element 1150 is connected to the closure piece by means of the coupling elements 1152 and 1154, which engage with the coupling elements 1140 and 1142 of the closure piece. Because of the connection of closure piece 1114 and expansion element 1150, the expansion element has also been pulled to the right and blocks the opening to the storage volume. A slot 1156 with which a deflecting unit (not shown in the figure) engages is also shown in this figure. The function of the deflecting unit is described elsewhere.

In part b) of the figure, the closure element 1114 has been moved to the left out of a central position by the actuator 1130. Because of the connection between the closure piece 1114 and expansion element 1150, the expansion element has also been moved to the left. The opening in the storage volume is now blocked in part by the closure piece 1114 and in part by the actuator 1130.

Figure 13:
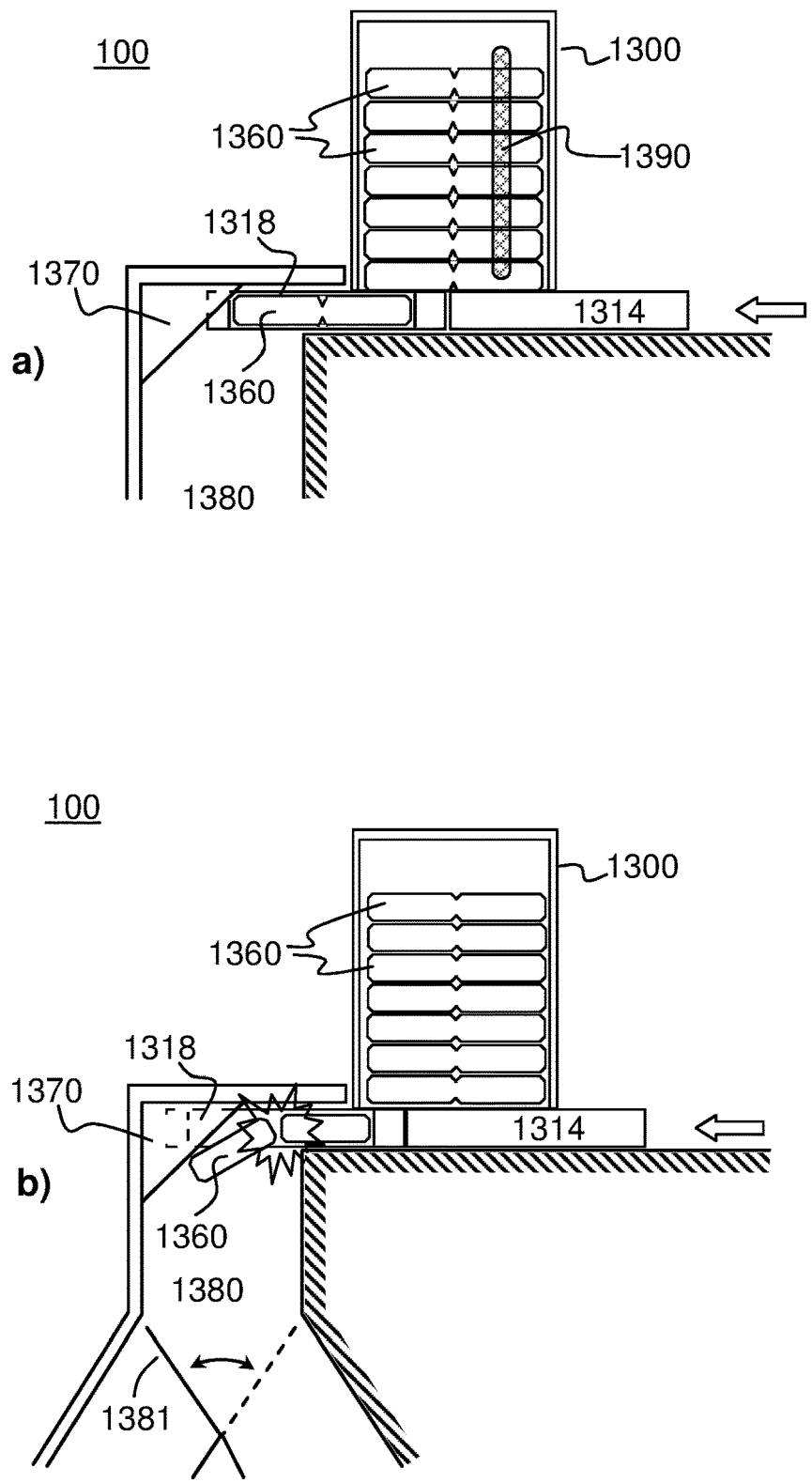
FIG. 13 shows a first schematic diagram of an apparatus, which makes it possible to discard a solid molded body or a part thereof in two stages.

FIG. 13 shows a first schematic diagram of an apparatus 100 which enables the supply or ejection of a solid molded body or a part thereof in two stages.

In part a) of the figure a solid molded body 1360 is accommodated in the recess or punched-out area 1318 of the closure piece 1314 of the ejector unit. Additional solid molded bodies 1360 are stored in the storage volume of the storage container 1300. Closure piece 1314 and solid molded body 1360 are moved in the direction of the arrow. In doing so, deflecting unit 1370 engages in the slot in the closure piece 1314. In this diagram, the solid molded body 1360 abuts against the deflecting unit 1370. The deflecting unit 1370 is a wedge or a triangular part of a feed channel 1380, for example, leading to a feed port in the mixing container (not shown in the figure). The figure also shows a transparent or translucent area 1390 on the storage container 1300 which permits visual monitoring of the filling level.

In part b) of the figure, solid molded bodies 1360 and closure piece 1314 are moved further in the direction of deflecting unit 1370. Deflecting unit 1370 here has blocked the movement of solid molded body 1360 and caused it to be broken along the intended breaking line. The part broken off falls into the feed channel 1380. A switch 1381 that can be switched between two outlets is provided in the feed channel 1380. One of the outlets leads to the mixing container (not shown in the figure) while the other leads to another container, also not shown, which accommodates solid molded bodies or parts thereof that are not used to prepare the solution.

In part b) of the figure, initially only a part of the solid molded body 1360 reaches the feed channel 1380. The other part remains in the recess or punched-out area 1318 in the closure piece 1314. When the closure piece 1314 is moved further to the right, the other part of the solid molded body 1360 also enters the feed channel where it is sent further by means of the switch 1381 either to the mixing container or to the additional container.

Figure 14:
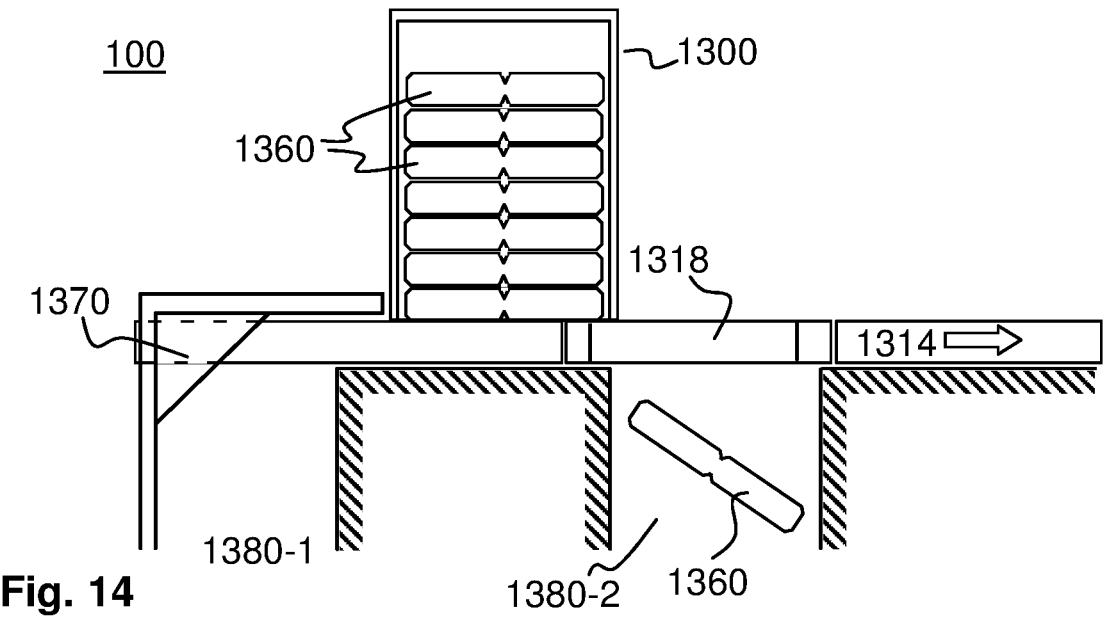
FIG. 14 shows a second schematic diagram of an apparatus, which makes it possible to discard a solid molded body or a part thereof.

FIG. 14 shows a second schematic diagram of an apparatus 100, which makes it possible for a solid molded body or a part thereof to be discarded. In the storage volume of the storage container 1300, solid molded bodies 1360 are stored; of these, one was accommodated in the recess or punched-out area 1318 of the closure piece 1314 and was moved to the right until it moved out of the recess or punched-out area 1318 of the closure piece 1314 via the right feed channel 1380-2 which leads to the additional container. In the same way, a solid molded body 1360 accommodated in the recess or punched-out area 1318 of the closure piece 1314 can be moved toward the left until it reaches the left feed channel 1380-1 which leads to the mixing container. The figure also shows a deflecting unit 1370, the function of which is explained with reference to FIG. 15. In this embodiment of the apparatus, no switch is necessary in the feed channel 1380-1. Feeding or ejecting take place through corresponding choice of direction in which the solid molded body 1360 is moved until it exits from the closure piece 1314.

Figure 15:
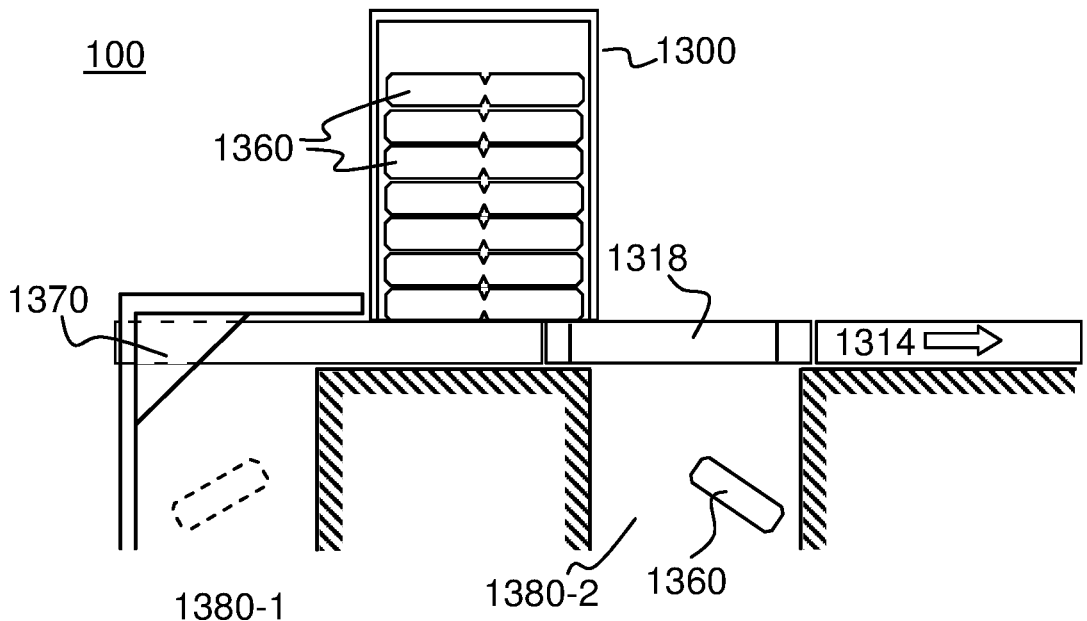
FIG. 15 shows a schematic diagram of the apparatus from FIG. 14 in supplying one part of a solid molded body and discarding another part.

FIG. 15 shows a schematic diagram of apparatus 100 from FIG. 14 in supplying a part of a solid molded body 1360. Solid molded body 1360 is conveyed as described with reference to FIG. 14, for example. As described with reference to FIG. 13, a solid molded body 1360 is broken on deflecting unit 1370 and enters the left feed channel 1380-1 leading to the mixing container. A remaining part of solid molded body 1360 is conveyed into the right feed channel 1380-2 through which it reaches the additional container.

Figure 16:
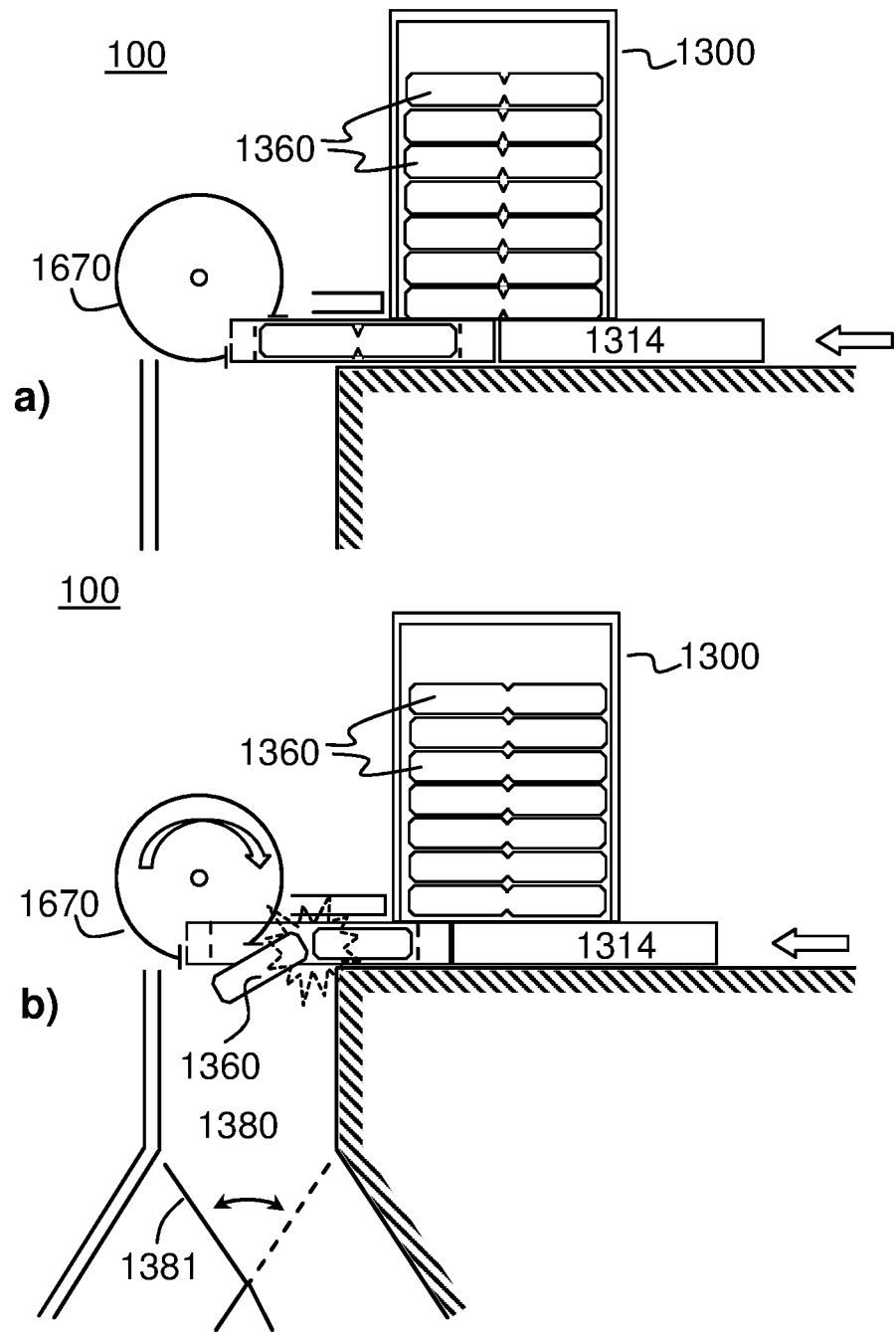
FIG. 16 shows a first schematic diagram of supplying one part of a solid molded body into two stages.

FIG. 16 shows a schematic diagram of another embodiment of apparatus 100 from FIG. 13. In this embodiment the deflecting unit 1670 is altered in comparison with that in FIG. 13. Instead of pressing the solid molded body against a stationary wedge until it breaks along the intended breaking line, in this embodiment the closure piece 1314 is pressed against a deflecting unit 1670, which is mounted so it can rotate about an axis and exerts a force on the solid body 1360 acting essentially at a right angle to the direction of displacement. In part a) of the figure, the closure piece 1314 has just come in contact with deflecting unit 1670. In part b) of the figure, the deflecting unit 1670 has already broken the solid molded body at the intended breaking line. For the sake of simplicity, deflecting unit 1670 is only shown schematically in the figure as part of a circle with stop surfaces, which come in contact with the closure piece 1314 and/or the solid molded body 1360. The arrow points in the direction of the rotation induced by displacement of the closure piece 1314. Part b) of FIG. 16 shows a situation comparable to that in part b) of FIG. 13. Deflecting unit 1670 has converted the linear movement of closure piece 1340 into a rotational movement, and the top part of the deflecting unit is pressing on the solid molded body 1360 and has broken it at the intended breaking line.

Figure 17:
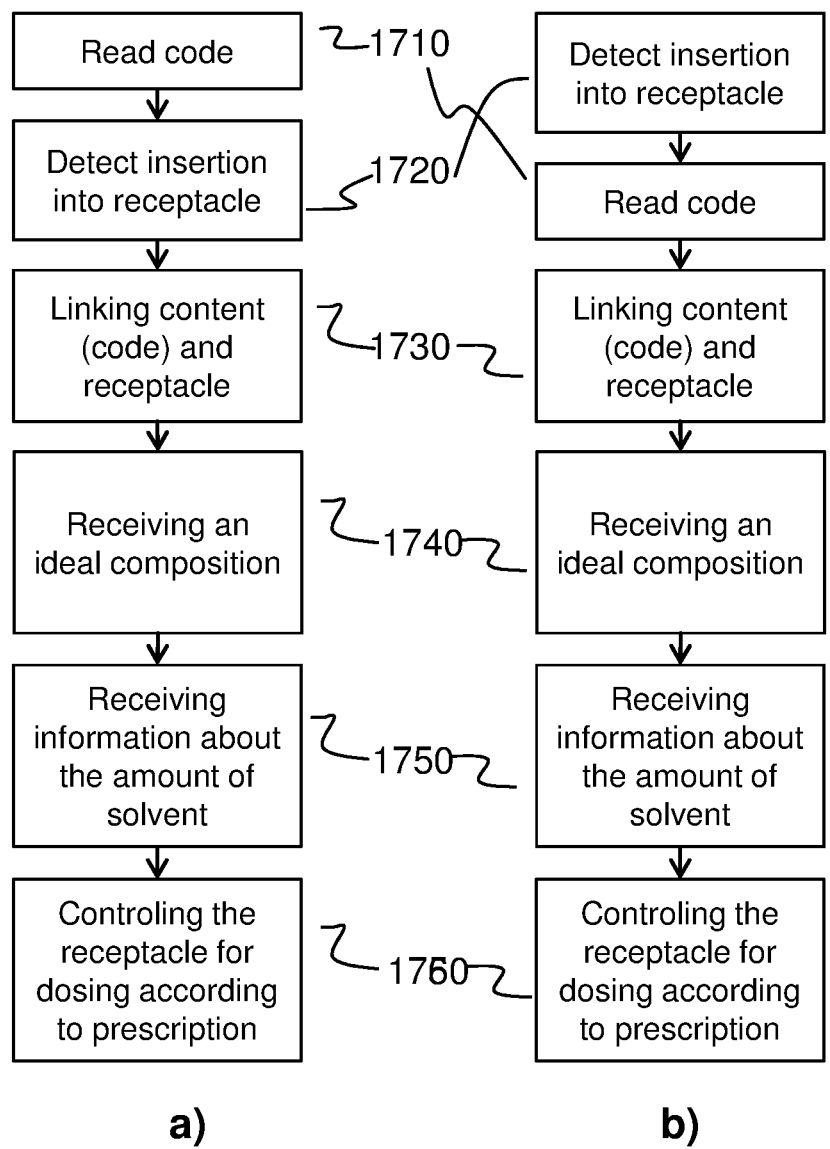
FIG. 17 shows the important steps of two alternative examples of methods for preparing a solution by means of the apparatus.

FIG. 17 shows as an example flowcharts of the main steps of two alternative exemplary methods 1700 for preparing a solution by means of the apparatus.

In part a) of the figure in step 1710, the code for a storage container is first read because it contains information about the ingredients of the solid molded bodies contained therein and optionally a sequence in which solid molded bodies with different ingredients and/or concentrations thereof can be removed. In step 1720, the insertion of the storage container into a corresponding receptacle in the apparatus is detected and a signal indicating this detection is generated and made available. The signal may also contain identification of the receptacle if the apparatus has a plurality of receptacles. In step 1730, the contents of the storage container and the identification of the receptacle are linked accordingly. In step 1740, the apparatus receives an ideal composition of the solution to be prepared, and in step 1750, it receives information about the amount of solvent and its properties. The term "properties" includes not only the type of solvent per se but also the basic mixture already present, if any, with specific ingredients. Then, in step 1760, the apparatus calculates from the available information the amount and optionally the type of solid molded bodies to be added to the solvent and controls the receptacle(s) of the apparatus in such a way that the desired composition of the solution is achieved.

In part b) of the figure, the steps 1710 and 1720 are exchanged in comparison with part a). The apparatus is then equipped to detect the code of a storage container that has already been inserted into a receptacle. This may take place, for example, by means of an electric and/or mechanical code contained in a base part of the storage container or it may be accomplished by optical detection of a code and/or detection of the code by electromagnetic waves over short distances. Detection of the insertion and coding may take place essentially simultaneously but this is not necessarily the case, for example, when only one actuator is provided for activation of an ejector, and different storage containers are connected individually and sequentially to the actuator. The other steps have already been described with reference to part a) and will not be explained again here.

Figure 18:
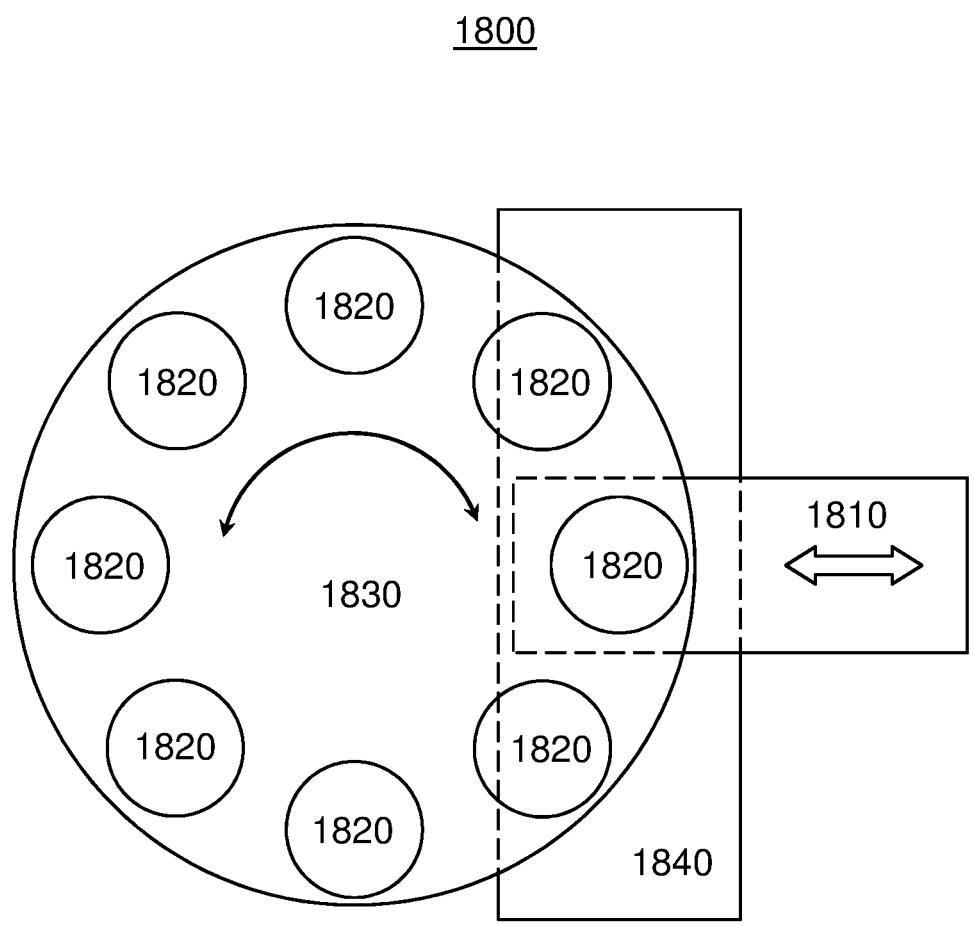
FIG. 18 shows a second schematic diagram of an example of an apparatus for preparing a solution.

FIG. 18 shows a top view of a second schematic diagram of an example of an apparatus 1800 for preparing a solution. In this example of an apparatus only one actuator 1810 is provided for actuation of an ejector (not shown in the figure) of the storage container 1820. To prepare the solution, one of a plurality of storage containers 1820 arranged so they can rotate on a carousel 1830 is brought to the position aligned with the actuator 1810. In this position, the actuator 1810 can activate the storage container 1820 to remove one or more solid molded bodies or parts thereof from the storage container 1820 and convey them into the mixing container 1840. The actuator and ejector may be the same or different in construction and may have the same or similar functioning as already described above.

LIST OF REFERENCE NUMERALS

100 apparatus
102 mixing container
104 inlet
106 outlet
108 solvent
110 cover part
112-115 receptacle for storage container
120-123 storage container
200 receptacle for storage container
202, 202-*x* coding detection device
402, 402-*x* coding detection device
600 receptacle for storage container
602 coding detection device
604 storage container
606 bays
700 storage container
702 base part
704, 706 barcode
710, 712 QR code
800, 800-*x* storage container
802 base part
804, 804-*x* storage volume
810 web
812 recess
814, 814-*x* closure piece
816, 816-*x* base body
818 recess/punched-out area
820 protrusion
822 depression
830, 830-*x* actuator
1100 storage container
1102 base part
1114 closure piece
1130 actuator
1140, 1142 recess
1144, 1146 coupling element
1150 expansion element
1152, 1154 coupling element
1156 slot
1300 storage container
1314 closure piece
1318 recess/punched-out area
1360 solid molded body
1370, 1670 deflecting unit
1380, 1380-*x* feed channel
1381 switch
1390 transparent/translucent area
1700-1760 method & method steps
1800 apparatus
1810 actuator
1820 storage container
1830 carousel
1840 mixing container

The invention claimed is:

1. An apparatus for preparing a medical solution by adding substances present in solid molded bodies to a solvent, comprising:

a mixing container having an inlet and an outlet, through which inlet the mixing container can be filled with a solvent, and out of which mixing container the solution can be supplied to an application via the outlet, and which also has a feed port, through which the solid molded bodies can be introduced into the mixing container, one or more storage containers accommodated by one or more corresponding receptacles, respectively, the one or more receptacles each having an actuator releasably connected to an ejector unit having a mobile closure piece of the one or more storage containers, respectively, as well as a dosing device located outside the mixing container and comprising the actuator releasably connected to the ejector unit having the mobile closure piece for controllable selective addition of solid molded bodies or parts thereof with different ingredients and/or different concentrations of ingredients from the one or more storage containers, which are supported in the one or more corresponding receptacles, wherein the solid molded bodies are stored in the one or more storage containers in such a way that they can be removed.

2. The apparatus according to claim 1, additionally comprising:

a code detection device for detecting and analyzing a machine-readable code connected to the one or more storage containers, respectively, said code containing information about which ingredients are contained in the solid molded bodies stored in the respective one or more storage containers.

3. The apparatus according to claim 2, wherein the code detection device comprises:

means for detecting the fact that the one or more storage containers is inserted into the one or more receptacles wherein the machine-readable code is provided by shaping of the one or more receptacles that accommodates only the one or more storage containers with the proper shape of the part to be received by the one or more receptacles, and/or a reader for reading out an optical code or an electrical code.

4. The apparatus according to claim 1, wherein the releasable connection between the actuator and the ejector unit permits a transfer of force from the actuator to the mobile closure piece of the ejector unit at least in one direction.

5. The apparatus according to claim 1, additionally comprising:

one or more units for ensuring the conveyance of solid molded bodies to an opening in the one or more storage containers connected to the apparatus.

6. The apparatus according to claim 1, wherein the mixing container is a disposable mixing container, additionally having:

a holder for removable accommodation of the disposable mixing container.

7. The apparatus according to claim 6, additionally having:

a guide device which automatically connects the inlet, the outlet and/or the feed port of the disposable mixing container to corresponding connections or openings on the apparatus, when the disposable mixing container is inserted into the apparatus, or which aligns the inlet, the outlet and/or the feed port relative to one another in such a way that their function is ensured.

8. The apparatus according to claim 1, additionally having of:

a device for introducing a gas into the mixing container.

9. The apparatus according to claim 4, wherein the dosing device has a selecting device by means of which solid molded bodies or parts thereof can optionally be conveyed into the mixing container or into an additional container.

10. The apparatus according to claim 9, (i) wherein the selecting device has a switch or an ejector, which switch or ejector is arranged upstream from the feed port of the mixing container or (ii) wherein the closure piece has an enlarged conveyance path over which a solid molded body or parts thereof can be conveyed into the additional container.

11. The apparatus according to claim 4 additionally having a deflecting device, which comes in contact with the solid molded body when the mobile closure piece has traveled a certain first distance in a first direction after removal of the solid molded body from the storage container, wherein the deflecting device exerts a force on at least one part of the solid molded body, acting in a second direction which points out of a first plane in which the first direction is located.

12. The apparatus according to claim 11, wherein the deflecting device is equipped to exert on contact a force on the solid molded body which causes at least first parts of the solid molded body to break off, wherein the dosing device or the mobile closure piece is designed so that second parts of the solid molded body cannot be moved in the second direction and/or in the opposite direction or can be moved only to an insignificant extent.

13. The apparatus according to claim 11, wherein the closure piece is equipped to ensure a certain orientation of the solid molded body with respect to the first direction during movement toward the deflecting device.

14. The apparatus according to claim 1, wherein a detection device is provided which signals that a solid molded body is ready in the dosing device.

15. The apparatus according to claim 14, wherein the detection device is equipped for optical and/or electrical detection and/or detection of a weight, a change in weight and/or a mechanical pulse.

16. The apparatus according to claim 1, additionally having a heating device for heating the mixing container.

17. The apparatus according to claim 1, additionally having a device for generating a flow in the mixing container.

* * * * *